(12) United States Patent
Gerlach et al.

(10) Patent No.: US 9,206,195 B2
(45) Date of Patent: Dec. 8, 2015

(54) DIHYDROTHIENOPYRIMIDINES

(75) Inventors: Kai Gerlach, Mittelbiberach (DE); Niklas Heine, Biberach an der Riss (DE); Scott Hobson, Mittelbiberach (DE); Christoph Hoenke, Ingelheim am Rhein (DE); Alexander Weber, Biberach an der Riss (DE)

(73) Assignee: Boehringer Ingelheim International GmbH, Ingelheim an Rhein (DE)

( * ) Notice: Subject to any disclaimer, the term of this patent is extended or adjusted under 35 U.S.C. 154(b) by 743 days.

(21) Appl. No.: 13/560,074

(22) Filed: Jul. 27, 2012

(65) Prior Publication Data

US 2013/0196988 A1    Aug. 1, 2013

(30) Foreign Application Priority Data

Aug. 9, 2011 (EP) .................................. 11176983
Sep. 22, 2011 (EP) .................................. 11182350

(51) Int. Cl.
*C07D 495/10* (2006.01)
*C07D 495/04* (2006.01)
*C07D 495/20* (2006.01)

(52) U.S. Cl.
CPC ............ *C07D 495/10* (2013.01); *C07D 495/04* (2013.01); *C07D 495/20* (2013.01)

(58) Field of Classification Search
CPC ..................................................... C07D 495/10
USPC ....................................... 514/234.2; 544/230
See application file for complete search history.

(56) References Cited

FOREIGN PATENT DOCUMENTS

WO    2010053438 A1    5/2010
WO    2011014535 A1    2/2011

OTHER PUBLICATIONS

International Search Report, for PCT/ISA/210, and Written Opinion, for PCT/ISA/237, for cooresponding application PCT/EP2012/065494, date of mailing Oct. 4, 2012.

*Primary Examiner* — Paul V Ward
(74) *Attorney, Agent, or Firm* — Michael P. Morris; Alan R. Stempel

(57) ABSTRACT

The present invention relates to dihydrothienopyrimidines, their use as modulators of γ-secretase and to pharmaceutical compositions containing said compounds. In particular, the present invention relates to compounds which interfere with γ-secretase and/or its substrate and therefore modulate the formation of Aβ peptides.

16 Claims, No Drawings

DIHYDROTHIENOPYRIMIDINES

FIELD OF THE INVENTION

The present invention relates to dihydrothienopyrimidines, their use as modulators of γ-secretase and to pharmaceutical compositions containing said compounds. In particular, the present invention relates to compounds which interfere with γ-secretase and/or its substrate and therefore modulate the formation of Aβ peptides. Accordingly these compounds can be used for the treatment of Aβ-related pathologies.

In addition, the invention relates to processes for preparing pharmaceutical compositions as well as compounds according to the invention.

BACKGROUND OF THE INVENTION

Alzheimer's disease (AD) is the most prevalent form of dementia. This neurodegenerative disorder is characterized by two major pathologies, β-amyloid deposits and neurofibrillary tangles. Clinically, AD is characterized by the loss of memory, cognition, reasoning, judgement as well as orientation. As the disease progresses, further abilities are lost until a global impairment of multiple cognitive functions occur. These cognitive losses take place gradually, but typically lead to severe impairment and eventual death in 4-12 years.

β-amyloid deposits are predominantly formed from aggregated Aβ peptide. The Aβ peptide is formed from amyloid precursor protein (APP) through two independent proteolytic events involving β-secretase followed by γ-secretase. Variability in the site of proteolysis via γ-secretase results in Aβ species of variable length, the most predominant forms of which are Aβ38, Aβ40 and Aβ42. The secreted Aβ then aggregates into oligomeric species, which further aggregate to ultimately form the Aβ deposits detected in the brains of AD patients. The aggregated oligomeric species are widely believed to be the key neurotoxic agent responsible for the neurodegeneration detected in the brains of AD patients. Of the various Aβ species generated by γ-secretase, Aβ42 has been demonstrated to be the most aggregation prone as well as the most neurotoxic Aβ species. Furthermore, human genetics strongly supports a key role of Aβ42 as a key mediator of AD pathogenesis. More than 150 different mutations causing familial AD are known which result from either an increase in the ratio of Aβ42/Aβ40 peptides produced or increase the intrinsic aggregation propensity of Aβ. Based on this knowledge, therapeutic approaches aimed at lowering levels of Aβ42 are considered promising.

β-amyloid deposits and vascular amyloid angiopathy have also been characterized in the brains of patients with Trisomy 21 (Down's Syndrome), Hereditary Cerebral Hemorrhage with Amyloidosis of the Dutch-type (HCHWA-D), and other neurodegenerative disorders.

γ-Secretase inhibitors completely inhibit the cleavage of APP as well as all other substrates of γ-secretase. This inhibition leads to a simultaneous inhibition of the production of all Aβ species. As opposed to γ-secretase inhibitors, γ-secretase modulators preferentially block the production of the neurotoxic Aβ42 species while not inhibiting APP cleavage and thereby the generation of all Aβ species. Furthermore, γ-Secretase modulators do not inhibit the cleavage of other γ-secretase substrates, thereby diminishing the possibility of side effects.

WO 2010/053438 discloses compounds of the following core structure

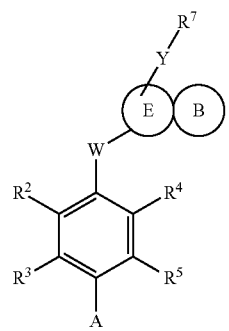

and their use as medicaments in the treatment of diseases like Alzheimer's disease. WO 2011/014535 discloses compounds of the following core structure

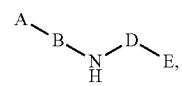

which modulate β-amyloid peptide production and their use in the treatment of Alzheimer's disease.

WO 2006/111549 discloses compounds of the following core structure

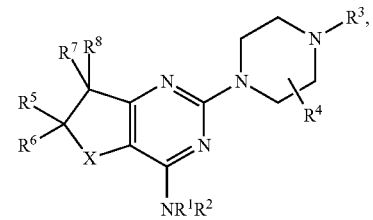

and their use as PDE4-inhibitors for the treatment of inflammatory diseases.

AIM OF THE INVENTION

It has now been found that compounds of the present invention according to general formula I are effective modulators of γ-secretase.

Accordingly, one aspect of the present invention relates to compounds according to formula I and salts thereof as modulators of γ-secretase.

A further aspect of the invention relates to the physiologically acceptable salts of the compounds of general formula I according to this invention with inorganic or organic acids.

In a further aspect this invention relates to pharmaceutical compositions, containing at least one compound according to formula I or a physiologically acceptable salt thereof, optionally together with one or more inert carriers and/or diluents.

A further aspect of the present invention relates to compounds according to formula I or a physiologically acceptable salt thereof or pharmaceutical compositions comprising compounds according to formula I or physiologically acceptable salts thereof for the use in the prevention and/or treatment of Aβ-related pathologies.

In a further aspect this invention relates to pharmaceutical compositions, containing at least one compound according to formula I or a physiologically acceptable salt thereof, optionally together with one or more inert carriers and/or diluents.

A further aspect of the present invention relates to compounds according to formula I or a physiologically acceptable salt thereof or pharmaceutical compositions comprising compounds according to formula I or physiologically acceptable salts thereof for the use in the prevention and/or treatment of diseases or conditions which can be influenced by modulating Aβ peptides, such as Aβ-related pathologies like Down's syndrome, Abeta-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, diffuse Lewy body type of Alzheimer's Disease, dementia of mixed vascular origin, dementia of degenerative origin, pre-senile dementia, senile dementia, dementia associated with Parkinson's disease, progressive supranuclear palsy or cortical basal degeneration, the dry form of age-related macular degeneration and glaucoma.

Other aims of the present invention will become apparent to the skilled man directly from the foregoing and following remarks.

DETAILED DESCRIPTION

In a first aspect the present invention relates to compounds of general formula I

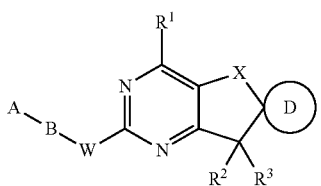

I wherein
A is selected from the group $A^a$ consisting of
a heteroaryl group with 5 or 6 ring atoms containing one to three heteroatoms independently selected from N, O, S,
wherein above mentioned heteroaryl groups may optionally be substituted with 1 or 2 substituents independently selected from the group consisting of halogen, cyano, $C_{1-6}$-alkyl- which is optionally fluorinated with 1 to 13 fluorine atoms, $C_{3-6}$-cycloalkyl-, $C_{1-4}$-alkyl-O—$C_{1-3}$-alkyl-, $C_{1-4}$-alkyl-O— which is optionally fluorinated with 1 to 9 fluorine atoms and $(C_{1-4}$-alkyl$)_3$Si—;
B is selected from the group $B^a$ consisting of

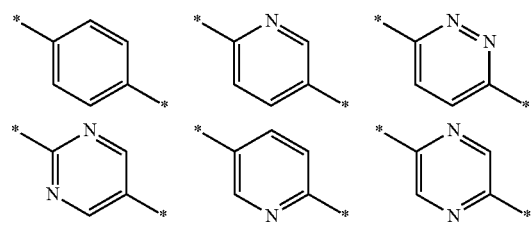

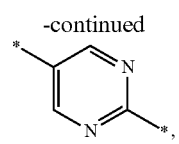

wherein above mentioned phenyl-, pyridinyl-, pyrimidinyl-, pyridazinyl and pyrazinyl groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms;
D is selected from the group $D^a$ consisting of
a mono- or bicyclic carbocyclus consisting of 3 to 10 carbon atoms
wherein one of the rings may be an aromatic ring, or
a 4- to 12-membered mono-, bicyclic or bridged heterocyclyl group,
wherein above mentioned ring $D^a$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, heterocyclyl, aryl, aryl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, aryl-C(O)—, $C_{1-4}$-alkyl-O—C(O)—, $(C_{1-4}$-alkyl$)_2$N—C(O)—, HO—, oxo, $C_{1-6}$-alkyl-O— which is optionally fluorinated with 1 to 13 fluorine atoms, $C_{3-6}$-cycloalkyl-O—, heterocyclyl-O—, aryl-O—, heteroaryl-O—, $H_2$N—, $(C_{1-4}$-alkyl$)_2$N—, azetidinyl, pyrrolidinyl and $(C_{1-4}$-alkyl)$(C_{1-3}$-alkyl-C(O))N—,
wherein above mentioned aryl-C(O)—, aryl-O—, aryl, aryl-$C_{1-3}$-alkyl-, heteroaryl, heteroaryl-$C_{1-3}$-alkyl- and heteroaryl-O— groups may optionally be substituted with 1 to 3 substituents independently selected from the group consisting of HO—, $C_{1-4}$-alkyl-O—, $F_3$CO—, $F_3$C—, $F_2$HCO—, FH$_2$CO—, heterocyclyl-O—, cyano, halogen, $F_5$S—, $(C_1$-$C_4$-alkyl$)_3$Si—, nitro, $H_2$N—, $(C_{1-4}$-alkyl$)_2$N—, $(H_2$N)—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl-which is optionally fluorinated with 1 to 13 fluorine atoms;
W is selected from the group $W^a$ consisting of
—(R$^7$)N— and —O—;
X is selected from the group $X^a$ consisting of
—S—, —S(O)— and —S(O)$_2$—;
R$^1$ is selected from the group $R^{1a}$ consisting of
H, $C_{1-6}$-alkyl-, $C_{2-6}$-alkenyl-, $C_{2-6}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, R$^4$R$^5$N—, R$^4$R$^5$N—$C_{1-3}$-alkyl- and R$^{40}$—,
wherein above mentioned $C_{2-6}$-alkenyl-, $C_{2-6}$-alkynyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, $C_{1-4}$-alkyl-O—, $F_3$CO—, $F_2$HCO—, FH$_2$CO—, heterocyclyl-O—, cyano, halogen, $F_5$S—, $(C_{1-4}$-alkyl$)_3$Si—, nitro, $H_2$N—, $(C_{1-4}$-alkyl$)_2$N—, $(H_2$N)—C(O)—, $(C_{1-4}$-alkyl)-HN—C(O)—, $(C_{1-4}$-alkyl$)_2$N—C(O)—, $C_{1-4}$-alkyl- O—$C_{1-4}$-alkyl- and $C_{1-6}$-alkyl- which is optionally fluorinated with 1 to 13 fluorine atoms, and wherein above mentioned $C_{1-6}$-alkyl-, carbocyclyl and carbocyclyl-$C_{1-3}$-alkyl-groups may optionally be substituted with 1 to 3 substituents independently selected from the group consisting of halogen, cyano, HO—, oxo, $C_{1-6}$-alkyl-, $C_{1-6}$-alkyl-O—, $C_{3-6}$-cycloalkyl-O—, oxetanyl-O—, tetrahydrofuryl-O— and tetrahydropyranyl-O—;

$R^2$, $R^3$ are selected independently of each other from the group $R^{2a}/R^{3a}$ consisting of H, halogen, $C_{1-6}$-alkyl-, $C_{3-6}$-cycloalkyl-, aryl, aryl-$C_{1-3}$-alkyl-, HO—, $C_{1-6}$-alkyl-O—, $C_{3-6}$-cycloalkyl-O—, wherein above mentioned aryl, and the aryl moiety of the aryl-$C_{1-3}$-alkyl-group may optionally be substituted with 1 to 3 substituents independently selected from the group consisting of HO—, $C_{1-4}$-alkyl-O—, heterocyclyl-O—, cyano, halogen, $F_5S$—, $(C_{1-4}$-alkyl$)_3Si$—, nitro, $H_2N$—, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms, and wherein the alkyl moieties of above mentioned $C_{1-6}$-alkyl-, $C_{3-6}$-cycloalkyl-, aryl-$C_{1-3}$-alkyl-, $C_{1-6}$-alkyl-O— and $C_{3-6}$-cycloalkyl-O-groups may optionally be substituted with 1 to 13 fluorine atoms, or $R^{2a}$ and $R^{3a}$ form together with the carbon atom to which they are attached an oxo group;

$R^4$, $R^5$ are selected independently of each other from the group $R^{4a}/R^{5a}$ consisting of H, $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl-, heterocyclyl-O—$C_{2-4}$-alkyl-, aryl, aryl-$C_{1-3}$-alkyl-, aryl-O—$C_{2-3}$-alkyl-, heteroaryl, heteroaryl-$C_{1-3}$-alkyl- and heteroaryl-O—$C_{2-3}$-alkyl-, wherein above mentioned $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl- or heterocyclyl-O—$C_{2-4}$-alkyl- groups may optionally be substituted with 1 to 3 substituents independently selected from the group consisting of halogen, cyano, HO—, oxo, $C_{1-4}$-alkyl-O— which is optionally fluorinated with 1 to 9 fluorine atoms, $C_{1-4}$-alkyl-O—C(O)—, HO—$C_{1-4}$-alkyl-, $C_{1-4}$-alkyl-O—$C_{1-4}$-alkyl-, heterocyclyl, $(C_{1-4}$-alkyl$)_2N$—, $(C_{1-3}$-alkyl$)_2N$—C(O)—, and $C_{1-6}$-alkyl- which is optionally fluorinated with 1 to 13 fluorine atoms, wherein above mentioned aryl-, aryl-$C_{1-3}$-alkyl-, aryl-O—$C_{2-3}$-alkyl-, heteroaryl-, heteroaryl-$C_{1-3}$-alkyl- and heteroaryl-O—$C_{2-3}$-alkyl- groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, $(R^6)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms, or $R^{4a}$ and $R^{5a}$ form together with the nitrogen atom to which they are attached a 4-12-membered mono-, bicyclic or bridged ring system optionally containing one or two double bonds and/or one aromatic ring and optionally containing one or two additional heteroatoms selected from the group consisting of —O—, —S—, —S(O)—, —S(O)$_2$—, —N($R^6$)—, wherein 2 geminal hydrogen atoms of the 4-12-membered mono- or bicyclic ring system may be replaced by a —(CH$_2$)$_{1-5}$— group and wherein one —(CH$_2$)— group of the —(CH$_2$)$_{1-5}$— group may be replaced by —O— or —N($R^6$)— and wherein above mentioned 4-12-membered mono-, bicyclic or bridged ring system may optionally be substituted with 1 or 2 substituents independently selected from the group consisting of halogen, cyano, aryl, heteroaryl, aryl-$C_{1-3}$-alkyl-, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, $C_{1-4}$-alkyl-O—C(O)—, HO—$C_{1-4}$-alkyl-, $C_{1-4}$-alkyl-O—$C_{1-4}$-alkyl-, $C_{3-6}$-cycloalkyl-O—$C_{1-4}$-alkyl-, heterocyclyl-O—, heterocyclyl-O—$C_{1-4}$-alkyl-, aryl-O—, heteroaryl-O— and $(R^6)_2N$—, wherein the directly above mentioned aryl, aryl-$C_{1-3}$-alkyl-, aryl-O—, heteroaryl-O—, and heteroaryl groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, amino, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms;

$R^6$ is selected independently of each other from the group $R^{6a}$ consisting of H, $C_{1-6}$-alkyl-, $C_{3-6}$-cycloalkyl, heterocyclyl, heteroaryl, HC(O)—, $C_{1-6}$-alkyl-C(O)—, $C_{3-6}$-cycloalkyl-C(O)—, aryl-C(O)—, $C_{1-4}$-alkyl-O—C(O)— and $(C_{1-4}$-alkyl$)_2N$—C(O)—, wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms and wherein the above mentioned aryl-C(O)— and heteroaryl group may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, amino, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl-which is optionally fluorinated with 1 to 13 fluorine atoms;

$R^7$ is selected independently of each other from the group $R^{7a}$ consisting of H, $C_{1-6}$-alkyl-, $C_{1-6}$-alkyl-C(O)— and $C_{1-6}$-alkyl-O—C(O)—, the tautomers thereof, the stereoisomers thereof, the mixtures thereof and the salts thereof.

Unless otherwise stated, the groups, residues, and substituents, particularly $R^1$, $R^2$, $R^3$, $R^4$, $R^5$, $R^6$, $R^7$, A, B, D, W and X are defined as above and hereinafter. If residues, substituents, or groups occur several times in a compound they may have the same or different meanings. Some preferred meanings of groups and substituents of the compounds according to the invention will be given hereinafter.

In a further embodiment of the present invention
A is selected from the group $A^b$ consisting of

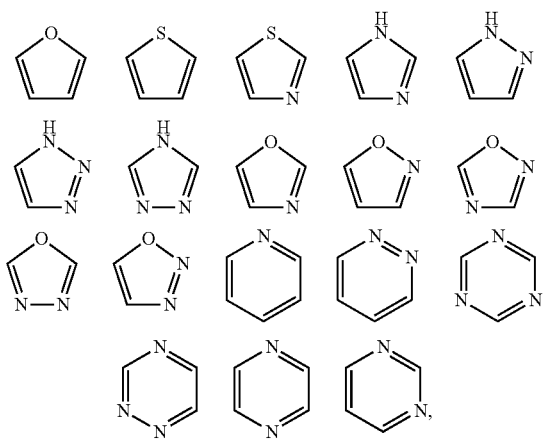

wherein above mentioned groups may optionally be substituted with 1 or 2 substituents independently selected from the group consisting of halogen, cyano, and $C_{1-6}$-alkyl- which is optionally fluorinated with 1 to 13 fluorine atoms.

In a further embodiment of the present invention
A is selected from the group $A^c$ consisting of

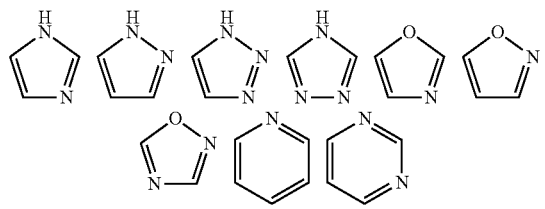

wherein above mentioned groups may optionally be substituted with 1 or 2 substituents independently selected from the group consisting of halogen and $C_{1-3}$-alkyl- which is optionally fluorinated with 1 to 7 fluorine atoms.

In a further embodiment of the present invention
A is selected from the group $A^d$ consisting of

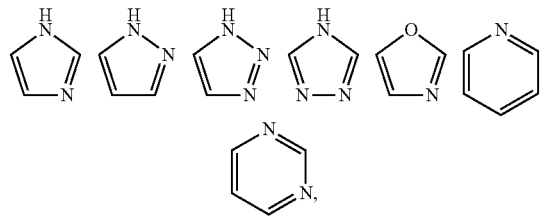

wherein above mentioned groups may optionally be substituted with 1 or 2 substituents independently selected from the group consisting of halogen and $C_{1-3}$-alkyl- which is optionally fluorinated with 1 to 7 fluorine atoms.

In a further embodiment of the present invention
B is selected from the group $B^b$ consisting of

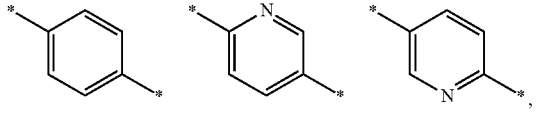

wherein above mentioned phenyl- and pyridinyl-groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms.

In a further embodiment of the present invention
B is selected from the group $B^c$ consisting of

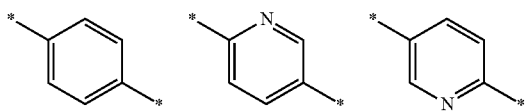

wherein above mentioned phenyl- and pyridinyl- groups may optionally be substituted with 1 or 2 substituents independently selected from the group consisting of halogen, cyano, $C_{1-3}$-alkyl-which is optionally fluorinated with 1 to 7 fluorine atoms, and $C_{1-3}$-alkyl-O— which is optionally fluorinated with 1 to 7 fluorine atoms.

In a further embodiment of the present invention
D is selected from the group $D^b$ consisting of

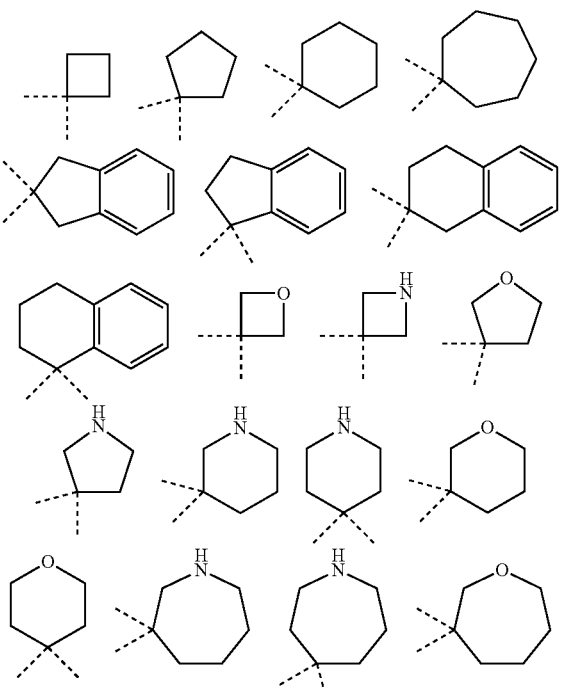

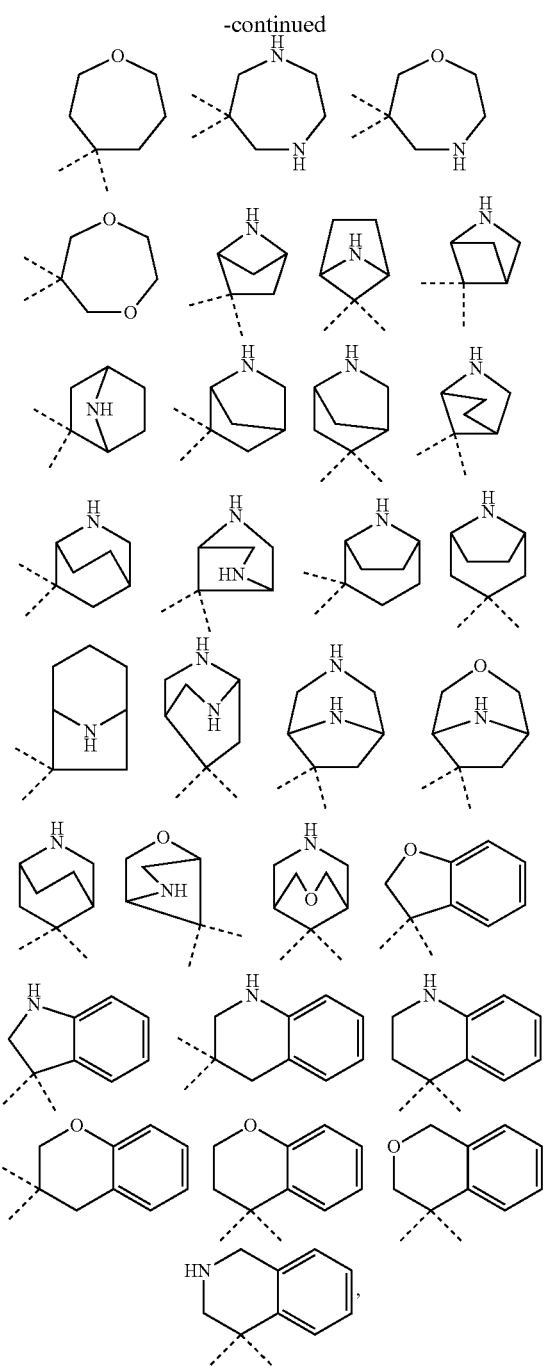

wherein above mentioned ring system D^b may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, heterocyclyl, aryl, aryl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, aryl-C(O)—, $C_{1-4}$-alkyl-O—C(O)—, $(C_{1-4}$-alkyl$)_2$N—C(O)—, HO—, oxo, $C_{1-6}$-alkyl-O— which is optionally fluorinated with 1 to 13 fluorine atoms, $C_{3-6}$-cycloalkyl-O—, heterocyclyl-O—, aryl-O—, heteroaryl-O—, $H_2N$—, $(C_{1-4}$-alkyl$)_2N$—, azetidinyl, pyrrolidinyl and $(C_{1-4}$-alkyl$)(C_{1-3}$-alkyl-C(O))N—, wherein above mentioned aryl-C(O)—, aryl-O—, aryl, aryl-$C_{1-3}$-alkyl-, heteroaryl, heteroaryl-$C_{1-3}$-alkyl- and heteroaryl-O— groups may optionally be substituted with 1 to 3 substituents independently selected from the group consisting of HO—, $C_{1-4}$-alkyl-O—, $F_3CO$—, $F_3C$—, $F_2HCO$—, $FH_2CO$—, heterocyclyl-O—, cyano, halogen, $F_5S$—, $(C_{1-4}$-alkyl$)_3Si$—, nitro, $H_2N$—, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl-which is optionally fluorinated with 1 to 13 fluorine atoms.

In a further embodiment of the present invention D is selected from the group $D^c$ consisting of

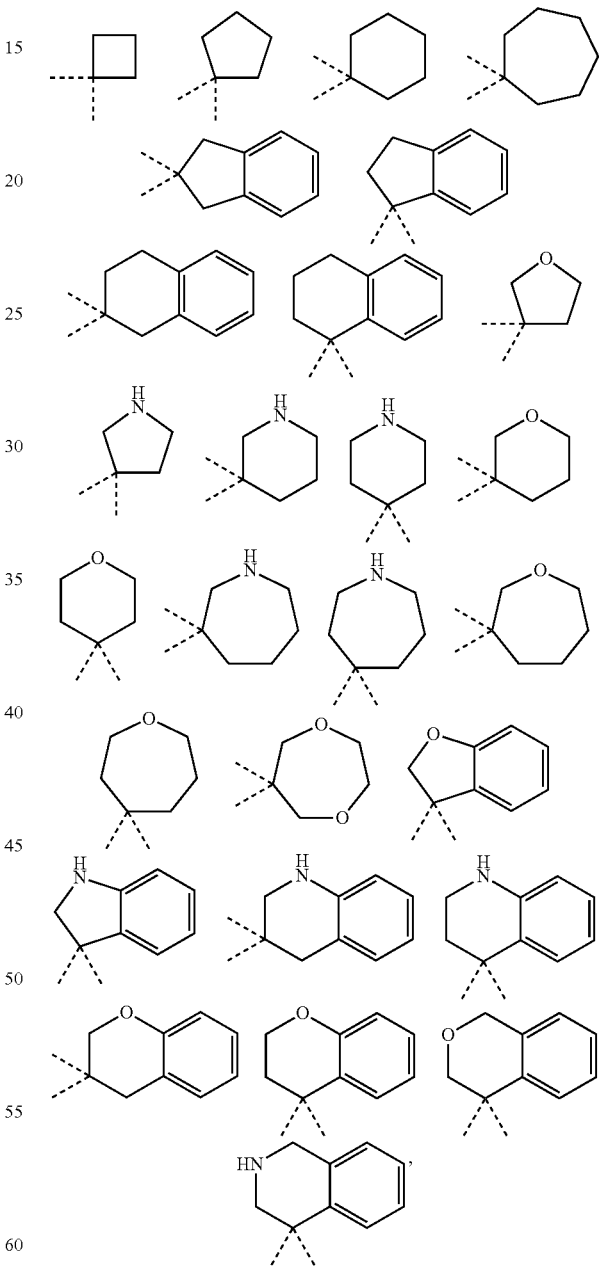

wherein above mentioned ring $D^c$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, oxetanyl, tetrahydrofuryl, tetrahydropyranyl, phenyl, phenyl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, phenyl-C(O)—, $C_{1-4}$-alkyl-O—C(O)—, ($C_{1-4}$-alkyl)$_2$N—C(O)—, HO—, oxo, $C_{1-6}$-alkyl-O-which is optionally fluorinated with 1 to 13 fluorine atoms, $C_{3-6}$-cycloalkyl-O—, oxetanyl-O—, tetrahydrofuryl-O—, tetrahydropyranyl-O—, phenyl-O—, heteroaryl-O—, H$_2$N—, ($C_{1-4}$-alkyl)$_2$N—, azetidinyl, pyrrolidinyl and ($C_{1-4}$-alkyl)($C_{1-3}$-alkyl-C(O))N—, wherein above mentioned phenyl, phenyl-$C_{1-3}$-alkyl-, heteroaryl-$C_{1-3}$-alkyl-, phenyl-C(O)—, phenyl-O—, heteroaryl- and heteroaryl-O-group may optionally be substituted with 1 to 3 substituents independently selected from the group consisting of HO—, $C_{1-4}$-alkyl-O—, F$_3$C—, F$_3$CO—, F$_2$HCO—, FH$_2$CO—, oxetanyl-O—, tetrahydrofuryl-O—, tetrahydropyranyl-O—, cyano, halogen, F$_5$S—, ($C_{1-4}$-alkyl)$_3$Si—, nitro, H$_2$N—, ($C_{1-4}$-alkyl)$_2$N—, (H$_2$N)—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl-which is optionally fluorinated with 1 to 13 fluorine atoms.

In a further embodiment of the present invention
D is selected from the group $D^d$ consisting of

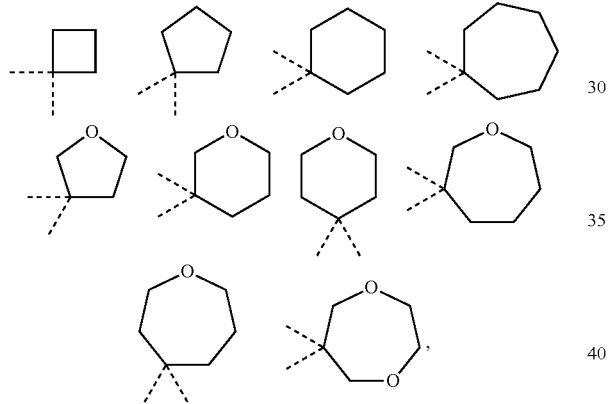

wherein above mentioned ring $D^d$ may optionally be substituted with 1 to 2 substituents independently selected from the group consisting of phenyl, phenyl-$C_{1-3}$-alkyl-, fluoro, $C_{1-6}$-alkyl- and $C_{1-3}$-alkyl-O—, wherein above mentioned phenyl and phenyl-$C_{1-3}$-alkyl- groups may optionally be substituted with 1 to 3 substituents independently selected from the group consisting of $C_{1-4}$-alkyl-O—, F$_3$C—, F$_3$CO—, F$_2$HCO—, FH$_2$CO—, cyano, halogen, and $C_{1-3}$-alkyl-.

In a further embodiment of the present invention
X is selected from the group $X^b$ consisting of
—S—, and —S(O)—.

In a further embodiment of the present invention
$R^1$ is selected from the group $R^{1b}$ consisting of
H, $C_{1-6}$-alkyl-, $C_{3-7}$-cycloalkyl-, $C_{3-7}$-cycloalkyl-$C_{1-3}$-alkyl-, C-linked heterocyclyl, heterocyclyl-$C_{1-3}$-alkyl-, aryl-$C_{1-3}$-alkyl-, heteroaryl-$C_{1-3}$-alkyl-, $R^4R^5N$—, $R^4R^5N$—$C_{1-3}$-alkyl- and $R^4O$—,
wherein above mentioned C-linked heterocyclyl, heterocyclyl-$C_{1-3}$-alkyl-, aryl-$C_{1-3}$-alkyl- and heteroaryl-$C_{1-3}$-alkyl-groups may optionally be substituted with 1 to 3 substituents independently selected from the group consisting of HO—, $C_{1-4}$-alkyl-O—, F$_3$CO—, F$_2$HCO—, FH$_2$CO—, heterocyclyl-O—, cyano, halogen, F$_5$S—, ($C_{1-4}$-alkyl)$_3$Si—, nitro, H$_2$N—, ($C_{1-4}$-alkyl)$_2$N—, (H$_2$N)—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl- which is optionally fluorinated with 1 to 13 fluorine atoms, and
wherein above mentioned $C_{1-6}$-alkyl-, $C_{3-7}$-cycloalkyl- and $C_{3-7}$-cycloalkyl-$C_{1-3}$-alkyl-groups may optionally be substituted with 1 to 3 substituents independently selected from the group consisting of halogen, cyano, HO—, oxo, $C_{1-6}$-alkyl-, $C_{1-6}$-alkyl-O—, $C_{3-6}$-cycloalkyl-O—, oxetanyl-O—, tetrahydrofuryl-O— and tetrahydropyranyl-O—.

In a further embodiment of the present invention
$R^1$ is selected from the group $R^{1c}$ consisting of
H, $R^4R^5N$—, $R^4R^5N$—$C_{1-3}$-alkyl- and $R^4O$—.

In a further embodiment of the present invention
$R^1$ is selected from the group $R^{1d}$ consisting of
H, $C_{1-6}$-alkyl-, $C_{3-7}$-cycloalkyl-, $C_{3-7}$-cycloalkyl-$C_{1-3}$-alkyl-, C-linked heterocyclyl, heterocyclyl-$C_{1-3}$-alkyl-, aryl-$C_{1-3}$-alkyl-, heteroaryl-$C_{1-3}$-alkyl-, $R^4R^5N$— and $R^4R^5N$—$C_{1-3}$-alkyl-,
wherein above mentioned C-linked heterocyclyl, heterocyclyl-$C_{1-3}$-alkyl-, aryl-$C_{1-3}$-alkyl- and heteroaryl-$C_{1-3}$-alkyl-groups may optionally be substituted with 1 to 3 substituents independently selected from the group consisting of HO—, $C_{1-4}$-alkyl-O—, F$_3$CO—, F$_2$HCO—, FH$_2$CO—, heterocyclyl-O—, cyano, halogen, F$_5$S—, ($C_{1-4}$-alkyl)$_3$Si—, nitro, H$_2$N—, ($C_{1-4}$-alkyl)$_2$N—, (H$_2$N)—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl- which is optionally fluorinated with 1 to 13 fluorine atoms, and
wherein above mentioned $C_{1-6}$-alkyl-, $C_{3-7}$-cycloalkyl- and $C_{3-7}$-cycloalkyl-$C_{1-3}$-alkyl-groups may optionally be substituted with 1 to 3 substituents independently selected from the group consisting of halogen, cyano, HO—, oxo, $C_{1-6}$-alkyl-, $C_{1-6}$-alkyl-O—, $C_{3-6}$-cycloalkyl-O—, oxetanyl-O—, tetrahydrofuryl-O— and tetrahydropyranyl-O—.

In a further embodiment of the present invention
$R^1$ is selected from the group $R^{1e}$ consisting of
H and $R^4R^5N$—.

In a further embodiment of the present invention
$R^2$, $R^3$ are selected independently of each other from the group $R^{2b}/R^{3b}$ consisting of
H, phenyl,
wherein above mentioned phenyl group may optionally be substituted with 1 to 3 substituents independently selected from the group consisting of $C_{1-4}$-alkyl-O—, cyano, halogen, F$_3$C— and $C_{1-6}$-alkyl-.

In a further embodiment of the present invention
$R^2$, $R^3$ are selected from the group $R^{2c}/R^{3c}$ consisting of
H.

In a further embodiment of the present invention
$R^4$, $R^5$ are selected independently of each other from the group $R^{4b}/R^{5b}$ consisting of
H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, heterocyclyl, heterocyclyl-$C_{1-6}$-alkyl-, aryl, aryl-$C_{1-3}$-alkyl-, aryl-O—$C_{2-3}$-alkyl-, heteroaryl and heteroaryl-$C_{1-3}$-alkyl-,
wherein above mentioned $C_{1-6}$-alkyl-, $C_{3-7}$-cycloalkyl-, $C_{3-7}$-cycloalkyl-$C_{1-3}$-alkyl-, $C_{3-7}$-cycloalkyl-O—$C_{2-4}$-alkyl-, heterocyclyl or heterocyclyl-$C_{1-6}$-alkyl-groups may optionally be substituted with 1 to 3 substituents independently selected from the group consisting of fluoro, HO—, oxo, $C_{1-4}$-alkyl-O— which is optionally fluorinated with 1 to 9 fluorine atoms, HO—$C_{1-4}$-alkyl-, $C_{1-4}$-alkyl-O—$C_{1-4}$-alkyl-, heterocyclyl, $(C_{1-3}$-alkyl$)_2$N—C(O)—, and $C_{1-6}$-alkyl- which is optionally fluorinated with 1 to 13 fluorine atoms, wherein above mentioned aryl-, aryl-$C_{1-3}$-alkyl-, aryl-O—$C_{2-3}$-alkyl-, heteroaryl- and heteroaryl-$C_{1-3}$-alkyl- groups may optionally be substituted with 1 to 3 substituents independently selected from the group consisting of $C_{1-4}$-alkyl-O—, $F_3CO$—, $F_2HCO$—, $FH_2CO$—, cyano, halogen, $(C_{1-4}$-alkyl$)_2$N—C(O)—, and $C_{1-6}$-alkyl- which is optionally fluorinated with 1 to 13 fluorine atoms, or $R^{4b}$ and $R^{5b}$ form together with the nitrogen atom to which they are attached a 4-12-membered mono-, bicyclic or bridged ring system optionally containing one double bond and/or one aromatic ring and optionally containing one additional heteroatom selected from the group consisting of —O—, —N($R^6$)—, wherein 2 geminal hydrogen atoms of the 4-12-membered mono- or bicyclic ring may be replaced by a —(CH$_2$)$_{1-5}$— group and wherein one —(CH$_2$)— group of the —(CH$_2$)$_{1-5}$— group may be replaced by —O— or —N($R^6$)— and wherein above mentioned 4-12-membered mono-, bicyclic or bridged ring system may optionally be substituted with 1 or 2 substituents independently selected from the group consisting of fluoro, aryl, heteroaryl, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, HO—$C_{1-4}$-alkyl-, $C_{1-4}$-alkyl-O—$C_{1-4}$-alkyl-, heterocyclyl-O— and ($R^6$)$_2$N—, wherein the directly above mentioned aryl and heteroaryl groups may optionally be substituted with 1 to 3 substituents independently selected from the group consisting of $C_{1-4}$-alkyl-O—, $F_3CO$—, $F_2HCO$—, $FH_2CO$—, cyano, halogen, $(C_{1-4}$-alkyl$)_2$N—C(O)— and $C_{1-6}$-alkyl-which is optionally fluorinated with 1 to 13 fluorine atoms.

In a further embodiment of the present invention $R^4$, $R^5$ are selected independently of each other from the group $R^{4c}/R^{5c}$ consisting of H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-, phenyl, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, triazinyl-$C_{1-3}$-alkyl-, wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl- or oxazepanyl-$C_{1-3}$-alkyl- groups may optionally be substituted with 1 to 3 substituents independently selected from the group consisting of fluoro, HO—, oxo, $C_{1-4}$-alkyl-O—, HO—$C_{1-4}$-alkyl-, $C_{1-4}$-alkyl-O—$C_{1-4}$-alkyl-, morpholinyl, oxetanyl, tetrahydrofuryl, tetrahydropyranyl, $(C_{1-3}$-alkyl$)_2$N—C(O)—, and $C_{1-6}$-alkyl- which is optionally fluorinated with 1 to 13 fluorine atoms, wherein above mentioned phenyl-, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, and triazinyl-$C_{1-3}$-alkyl- groups may optionally be substituted with 1 to 3 substituents independently selected from the group consisting of $C_{1-3}$-alkyl-, $F_3C$—, $C_{1-4}$-alkyl-O—, $F_3CO$—, $F_2HCO$—, $FH_2CO$—, cyano and halogen, or $R^{4c}$ and $R^{6c}$ form together with the nitrogen atom to which they are attached a 4-11-membered mono-, bicyclic or bridged ring system optionally containing one aromatic ring and optionally one additional heteroatom selected from the group consisting of —O—, —N($R^6$)—, wherein 2 geminal hydrogen atoms of the 4-11-membered saturated mono- or bicyclic ring may be replaced by a —(CH$_2$)$_{1-5}$— group and wherein one —(CH$_2$)— group of the —(CH$_2$)$_{1-5}$— group may be replaced by —O— or —N($R^6$)— and wherein above mentioned 4-11-membered mono-, bicyclic or bridged ring system may optionally be substituted with 1 or 2 substituents independently selected from the group consisting of fluoro, aryl, heteroaryl, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, HO—$C_{1-4}$-alkyl-, $C_{1-4}$-alkyl-O—$C_{1-4}$-alkyl-, heterocyclyl-O—, ($R^6$)$_2$N—;

wherein the directly above mentioned aryl and heteroaryl groups may optionally be substituted with 1 to 3 substituents independently selected from the group consisting of $C_{1-4}$-alkyl-O—, $F_3CO$—, $F_2HCO$—, $FH_2CO$—, cyano, halogen, $(C_{1-4}$-alkyl$)_2$N—C(O)— and $C_{1-6}$-alkyl-which is optionally fluorinated with 1 to 13 fluorine atoms.

In a further embodiment of the present invention $R^4$, $R^5$ are selected independently of each other from the group $R^{4d}/R^{5d}$ consisting of H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-, phenyl, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, triazinyl-$C_{1-3}$-alkyl-, wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl- or tetrahydropyranyl-$C_{1-3}$-alkyl- groups may optionally be substituted with 1 to 3 substituents independently selected from the group consisting of fluoro, HO—, oxo, $C_{1-4}$-alkyl-O—, HO—$C_{1-4}$-alkyl-, $C_{1-4}$-alkyl-O—$C_{1-4}$-alkyl-, oxetanyl, tetrahydrofuryl, tetrahydropyranyl, and $C_{1-6}$-alkyl- which is optionally fluorinated with 1 to 13 fluorine atoms, wherein above mentioned phenyl-, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-pyrimidinyl-$C_{1-3}$-alkyl- and triazinyl-$C_{1-3}$-alkyl- groups may optionally be substituted with 1 to 3 substituents independently selected from the group consisting of $C_{1-3}$-alkyl-, $F_3C$—, $C_{1-4}$-alkyl-O—, $F_3CO$—, $F_2HCO$—, $FH_2CO$—, cyano and halogen, or $R^{4d}$ and $R^{5d}$ form together with the nitrogen atom to which they are attached a ring system selected from the group consisting of,

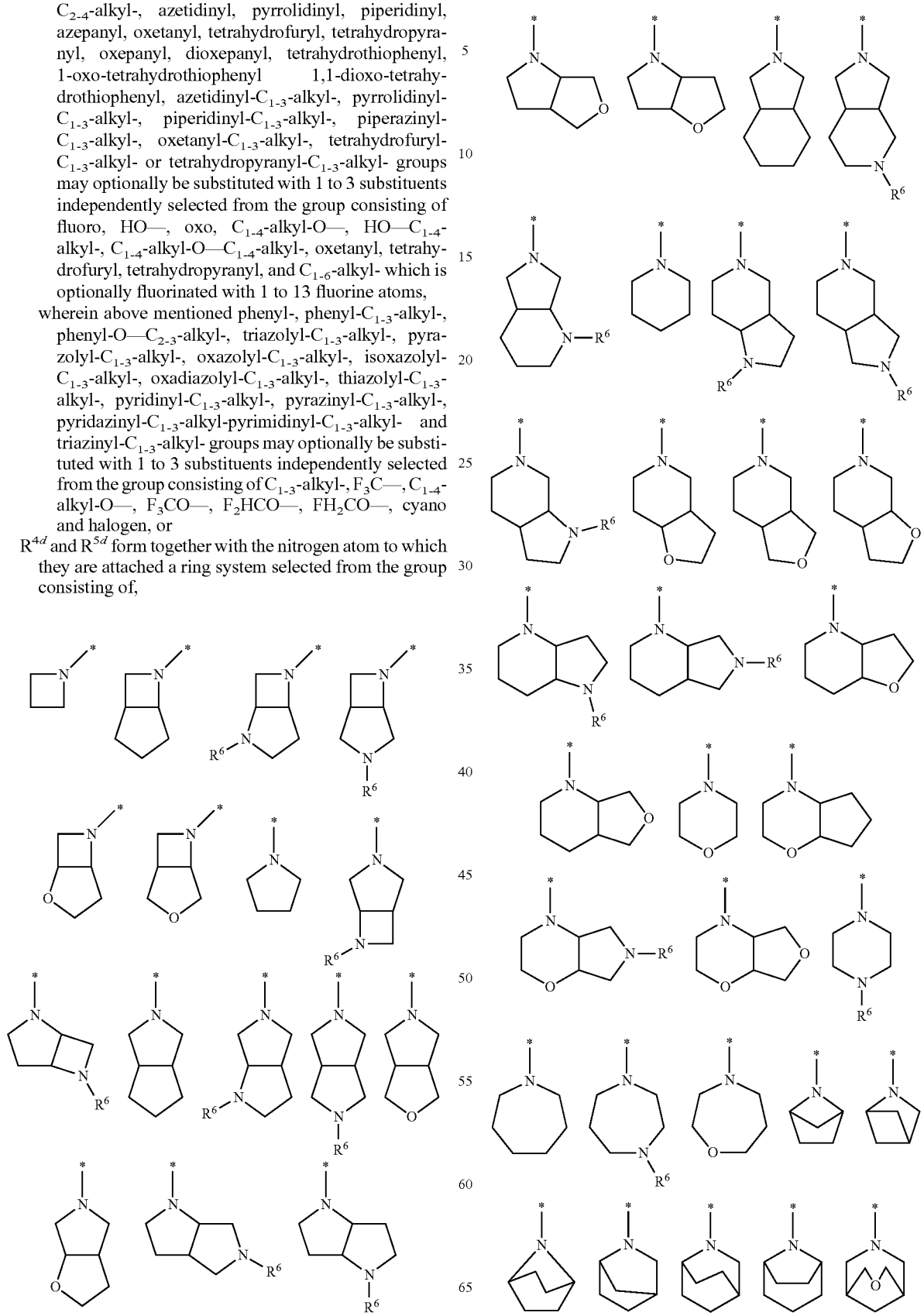

-continued

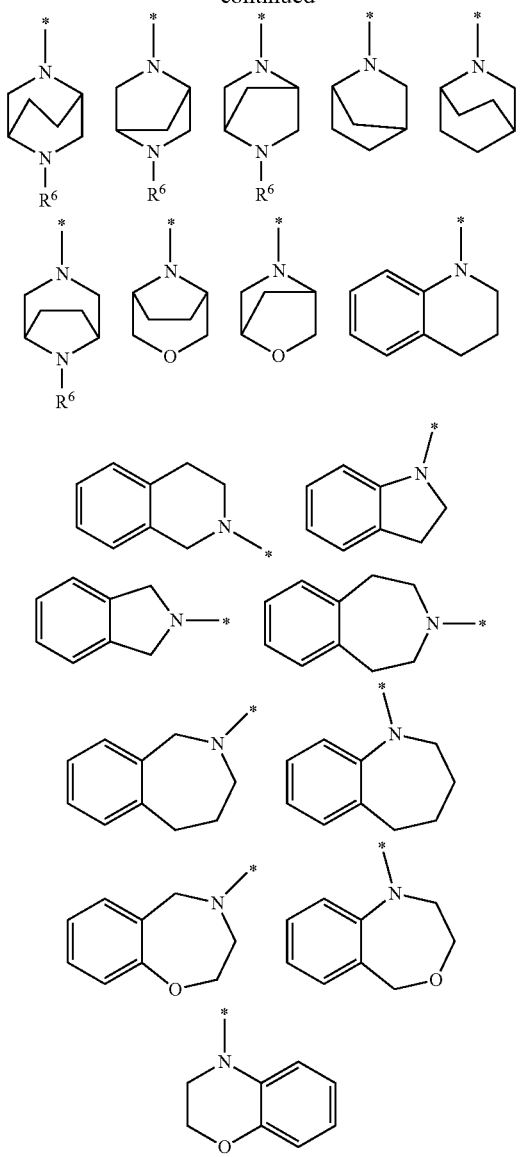

wherein 2 geminal hydrogen atoms of the above mentioned mono- or bicyclic ring may be replaced by a —$(CH_2)_{3-5}$— group and
wherein one —$(CH_2)$— group of the —$(CH_2)_{3-5}$— group may be replaced by —O— or —$N(R^6)$— and
wherein above mentioned mono- or bicyclic ring may optionally be substituted with 1 or 2 substituents independently selected from the group consisting of fluoro, phenyl, $C_{1-6}$-alkyl- which is optionally fluorinated with 1 to 13 fluorine atoms, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, HO—, oxo, $C_{1-6}$-alkyl-O—, $C_{3-6}$-cycloalkyl-O—, HO—$C_{1-4}$-alkyl-, $C_{1-4}$-alkyl-O—$C_{1-4}$-alkyl-, oxetanyl-O—, tetrahydrofuryl-O—, tetrahydropyranyl-O— and $(R^6)_2N$—
wherein the aforementioned phenyl groups may optionally be substituted with 1 to 3 substituents independently selected from the group consisting of $F_3C$—, $C_{1-4}$-alkyl-O—, $F_3CO$—, $F_2HCO$—, $FH_2CO$—, cyano, halogen, and $C_{1-3}$-alkyl-.

In a further embodiment of the present invention $R^6$ is selected independently of each other from the group $R^{6b}$ consisting of H, $C_{1-6}$-alkyl-, $C_{3-6}$-cycloalkyl, oxetanyl, tetrahydrofuryl, tetrahydropyranyl, pyridinyl, pyrimidinyl, pyridazinyl, pyrazinyl, triazinyl, thiazolyl, oxadiazolyl, oxazolyl, HC(O)—, $C_{1-6}$-alkyl-C(O)—, $C_{3-6}$-cycloalkyl-C(O)—, phenyl-C(O)—, $C_{1-4}$-alkyl-O—C(O)— and $(C_{1-4}$-alkyl$)_2$N—C(O)—,
wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms and
wherein the aforementioned phenyl-C(O)—, pyridinyl, pyrimidinyl, pyridazinyl, pyrazinyl, triazinyl, thiazolyl oxadiazolyl and oxazolyl groups may optionally be substituted with 1 to 3 substituents independently selected from the group consisting of $C_{1-4}$-alkyl-O—, $F_3C$—, $F_3CO$—, $F_2HCO$—, $FH_2CO$—, cyano, halogen, and $C_{1-3}$-alkyl-.

In a further embodiment of the present invention $R^7$ is selected independently of each other from the group $R^{7b}$ consisting of H.

Each $R^{1x}$, $R^{2x/3x}$, $R^{4x/5x}$, $R^{6x}$, $R^{7x}$, $A^x$, $B^x$, $D^x$, $W^x$ and $X^x$ represents a characterized, individual embodiment for the corresponding substituent as described above. Thus given the above definitions, preferred individual embodiments of the first aspect of the invention are fully characterized by the term $R^{1x}$, $R^{2x/3x}$, $R^{4x/5x}$, $R^{6x}$, $R^{7x}$, $A^x$, $B^x$, $D^x$, $W^x$ and $X^x$), wherein for each index x an individual figure is given that ranges from "a" to the highest letter given above. All individual embodiments described by the term in parentheses with full permutation of the indices x, referring to the definitions above, shall be comprised by the present invention.

The following Table 1 shows, exemplarily and in the order of increasing preference from the first line to the last line, such embodiments E-1 to E-24 of the invention that are considered preferred. This means that embodiment E-24, represented by the entries in the last row of Table 1, is the most preferred embodiment.

TABLE 1

Preferred embodiments E-1 to E-24 of the invention

|  | A | B | D | W | X | $R^1$ | $R^2/R^3$ | $R^4/R^5$ | $R^6$ | $R^7$ |
|---|---|---|---|---|---|---|---|---|---|---|
| E-1 | $A^b$ | $B^b$ | $D^b$ | $W^a$ | $X^a$ | $R^{1b}$ | $R^{2b}/R^{3b}$ | $R^{4b/5b}$ | $R^{6b}$ | $R^{7b}$ |
| E-2 | $A^c$ | $B^b$ | $D^b$ | $W^a$ | $X^a$ | $R^{1b}$ | $R^{2c}/R^{3c}$ | $R^{4c/5c}$ | $R^{6b}$ | $R^{7b}$ |
| E-3 | $A^b$ | $B^c$ | $D^c$ | $W^a$ | $X^a$ | $R^{1e}$ | $R^{2b}/R^{3b}$ | $R^{4b/5b}$ | $R^{6b}$ | $R^{7b}$ |
| E-4 | $A^c$ | $B^c$ | $D^c$ | $W^a$ | $X^a$ | $R^{1e}$ | $R^{2c}/R^{3c}$ | $R^{4c/5c}$ | $R^{6b}$ | $R^{7b}$ |
| E-5 | $A^d$ | $B^c$ | $D^c$ | $W^a$ | $X^a$ | $R^{1c}$ | $R^{2c}/R^{3c}$ | $R^{4a/5a}$ | $R^{6b}$ | $R^{7b}$ |
| E-6 | $A^d$ | $B^c$ | $D^c$ | $W^a$ | $X^a$ | $R^{1c}$ | $R^{2c}/R^{3c}$ | $R^{4b/5b}$ | $R^{6b}$ | $R^{7b}$ |
| E-7 | $A^d$ | $B^c$ | $D^c$ | $W^a$ | $X^a$ | $R^{1c}$ | $R^{2c}/R^{3c}$ | $R^{4c/5c}$ | $R^{6b}$ | $R^{7b}$ |
| E-8 | $A^d$ | $B^c$ | $D^c$ | $W^a$ | $X^a$ | $R^{1c}$ | $R^{2c}/R^{3c}$ | $R^{4d/5d}$ | $R^{6b}$ | $R^{7b}$ |
| E-9 | $A^d$ | $B^c$ | $D^c$ | $W^a$ | $X^a$ | $R^{1d}$ | $R^{2c}/R^{3c}$ | $R^{4a/5a}$ | $R^{6b}$ | $R^{7b}$ |
| E-10 | $A^d$ | $B^c$ | $D^c$ | $W^a$ | $X^a$ | $R^{1d}$ | $R^{2c}/R^{3c}$ | $R^{4b/5b}$ | $R^{6b}$ | $R^{7b}$ |
| E-11 | $A^d$ | $B^c$ | $D^c$ | $W^a$ | $X^a$ | $R^{1d}$ | $R^{2c}/R^{3c}$ | $R^{4c/5c}$ | $R^{6b}$ | $R^{7b}$ |
| E-12 | $A^d$ | $B^c$ | $D^c$ | $W^a$ | $X^a$ | $R^{1d}$ | $R^{2c}/R^{3c}$ | $R^{4d/5d}$ | $R^{6b}$ | $R^{7b}$ |
| E-13 | $A^d$ | $B^c$ | $D^c$ | $W^a$ | $X^a$ | $R^{1e}$ | $R^{2c}/R^{3c}$ | $R^{4d/5d}$ | $R^{6b}$ | $R^{7b}$ |
| E-14 | $A^d$ | $B^c$ | $D^c$ | $W^a$ | $X^b$ | $R^{1e}$ | $R^{2c}/R^{3c}$ | $R^{4d/5d}$ | $R^{6b}$ | $R^{7b}$ |
| E-15 | $A^d$ | $B^c$ | $D^d$ | $W^a$ | $X^a$ | $R^{1c}$ | $R^{2c}/R^{3c}$ | $R^{4a/5a}$ | $R^{6b}$ | $R^{7b}$ |
| E-16 | $A^d$ | $B^c$ | $D^d$ | $W^a$ | $X^a$ | $R^{1c}$ | $R^{2c}/R^{3c}$ | $R^{4b/5b}$ | $R^{6b}$ | $R^{7b}$ |
| E-17 | $A^d$ | $B^c$ | $D^d$ | $W^a$ | $X^a$ | $R^{1c}$ | $R^{2c}/R^{3c}$ | $R^{4c/5c}$ | $R^{6b}$ | $R^{7b}$ |
| E-18 | $A^d$ | $B^c$ | $D^d$ | $W^a$ | $X^a$ | $R^{1c}$ | $R^{2c}/R^{3c}$ | $R^{4d/5d}$ | $R^{6b}$ | $R^{7b}$ |
| E-19 | $A^d$ | $B^c$ | $D^d$ | $W^a$ | $X^a$ | $R^{1d}$ | $R^{2c}/R^{3c}$ | $R^{4a/5a}$ | $R^{6b}$ | $R^{7b}$ |
| E-20 | $A^d$ | $B^c$ | $D^d$ | $W^a$ | $X^a$ | $R^{1d}$ | $R^{2c}/R^{3c}$ | $R^{4b/5b}$ | $R^{6b}$ | $R^{7b}$ |
| E-21 | $A^d$ | $B^c$ | $D^d$ | $W^a$ | $X^a$ | $R^{1d}$ | $R^{2c}/R^{3c}$ | $R^{4c/5c}$ | $R^{6b}$ | $R^{7b}$ |
| E-22 | $A^d$ | $B^c$ | $D^d$ | $W^a$ | $X^a$ | $R^{1d}$ | $R^{2c}/R^{3c}$ | $R^{4d/5d}$ | $R^{6b}$ | $R^{7b}$ |

TABLE 1-continued

Preferred embodiments E-1 to E-24 of the invention

| | A | B | D | W | X | $R^1$ | $R^2/R^3$ | $R^4/R^5$ | $R^6$ | $R^7$ |
|---|---|---|---|---|---|---|---|---|---|---|
| E-23 | $A^d$ | $B^c$ | $D^d$ | $W^a$ | $X^a$ | $R^{1e}$ | $R^{2c}/R^{3c}$ | $R^{4d/5d}$ | $R^{6b}$ | $R^{7b}$ |
| E-24 | $A^d$ | $B^c$ | $D^d$ | $W^a$ | $X^b$ | $R^{1e}$ | $R^{2c}/R^{3c}$ | $R^{4d/5d}$ | $R^{6b}$ | $R^{7b}$ | the tautomers thereof, the stereoisomers thereof, the mixtures thereof, and the salts thereof, Accordingly, for example E-24 covers compounds of formula I, wherein A is selected from the group $A^d$ consisting of

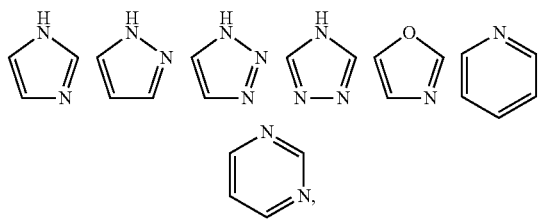

wherein above mentioned groups may optionally be substituted with 1 or 2 substituents independently selected from the group consisting of halogen and $C_{1-3}$-alkyl- which is optionally fluorinated with 1 to 7 fluorine atoms, B is selected from the group $B^c$ consisting of

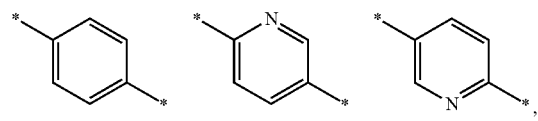

wherein above mentioned phenyl- and pyridinyl- groups may optionally be substituted with 1 or 2 substituents independently selected from the group consisting of halogen, cyano, $C_{1-3}$-alkyl-which is optionally fluorinated with 1 to 7 fluorine atoms, and $C_{1-3}$-alkyl-O— which is optionally fluorinated with 1 to 7 fluorine atoms, D is selected from the group $D^d$ consisting of

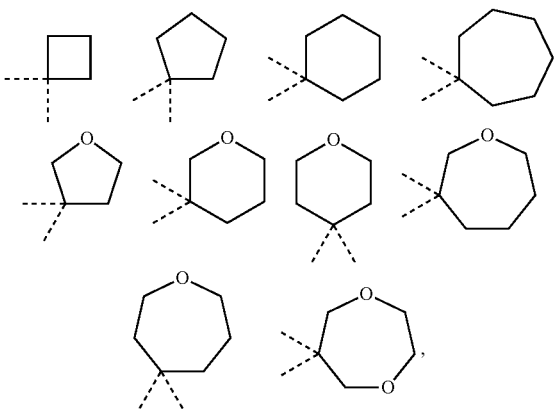

wherein above mentioned ring $D^d$ may optionally be substituted with 1 to 2 substituents independently selected from the group consisting of phenyl, phenyl-$C_{1-3}$-alkyl-, fluoro, $C_{1-6}$-alkyl- and $C_{1-3}$-alkyl-O—, wherein above mentioned phenyl and phenyl-$C_{1-3}$-alkyl- groups may optionally be substituted with 1 to 3 substituents independently selected from the group consisting of $C_{1-4}$-alkyl-O—, $F_3C$—, $F_3CO$—, $F_2HCO$—, $FH_2CO$—, cyano, halogen, and $C_{1-3}$-alkyl-, W is selected from the group $W^a$ consisting of
—($R^7$)N— and O—, X is selected from the group $X^b$ consisting of
—S—, and —S(O)—, $R^1$ is selected from the group $R^{1e}$ consisting of
H and $R^4R^5N$—, $R^2$, $R^3$ are selected from the group $R^{2c}/R^{3c}$ consisting of
H, $R^4$, $R^5$ are selected independently of each other from the group $R^{4d}/R^{5d}$ consisting of H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl-, tetrahydropyranyl-$C_{1-3}$-alkyl-, phenyl, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-, pyrimidinyl-$C_{1-3}$-alkyl-, triazinyl-$C_{1-3}$-alkyl-, wherein above mentioned $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, azetidinyl-$C_{1-3}$-alkyl-, pyrrolidinyl-$C_{1-3}$-alkyl-, piperidinyl-$C_{1-3}$-alkyl-, piperazinyl-$C_{1-3}$-alkyl-, oxetanyl-$C_{1-3}$-alkyl-, tetrahydrofuryl-$C_{1-3}$-alkyl- or tetrahydropyranyl-$C_{1-3}$-alkyl- groups may optionally be substituted with 1 to 3 substituents independently selected from the group consisting of fluoro, HO—, oxo, $C_{1-4}$-alkyl-O—, HO—$C_{1-4}$-alkyl-, $C_{1-4}$-alkyl-O—$C_{1-4}$-alkyl-, oxetanyl, tetrahydrofuryl, tetrahydropyranyl, and $C_{1-6}$-alkyl- which is optionally fluorinated with 1 to 13 fluorine atoms, wherein above mentioned phenyl-, phenyl-$C_{1-3}$-alkyl-, phenyl-O—$C_{2-3}$-alkyl-, triazolyl-$C_{1-3}$-alkyl-, pyrazolyl-$C_{1-3}$-alkyl-, oxazolyl-$C_{1-3}$-alkyl-, isoxazolyl-$C_{1-3}$-alkyl-, oxadiazolyl-$C_{1-3}$-alkyl-, thiazolyl-$C_{1-3}$-alkyl-, pyridinyl-$C_{1-3}$-alkyl-, pyrazinyl-$C_{1-3}$-alkyl-, pyridazinyl-$C_{1-3}$-alkyl-pyrimidinyl-$C_{1-3}$-alkyl- and triazinyl-$C_{1-3}$-alkyl- groups may optionally be substituted with 1 to 3 substituents independently selected from the group consisting of $C_{1-3}$-alkyl-, $F_3C$—, $C_{1-4}$-alkyl-O—, $F_3CO$—, $F_2HCO$—, $FH_2CO$—, cyano and halogen, or $R^{4d}$ and $R^{5d}$ form together with the nitrogen atom to which they are attached a ring system selected from the group consisting of,

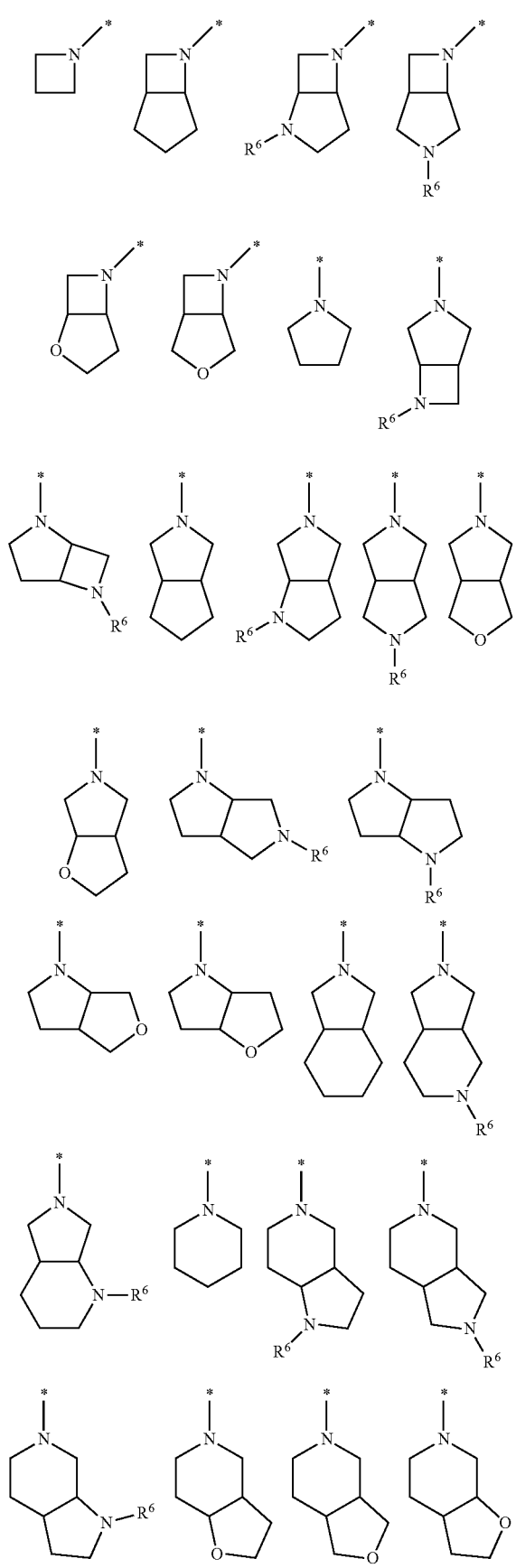
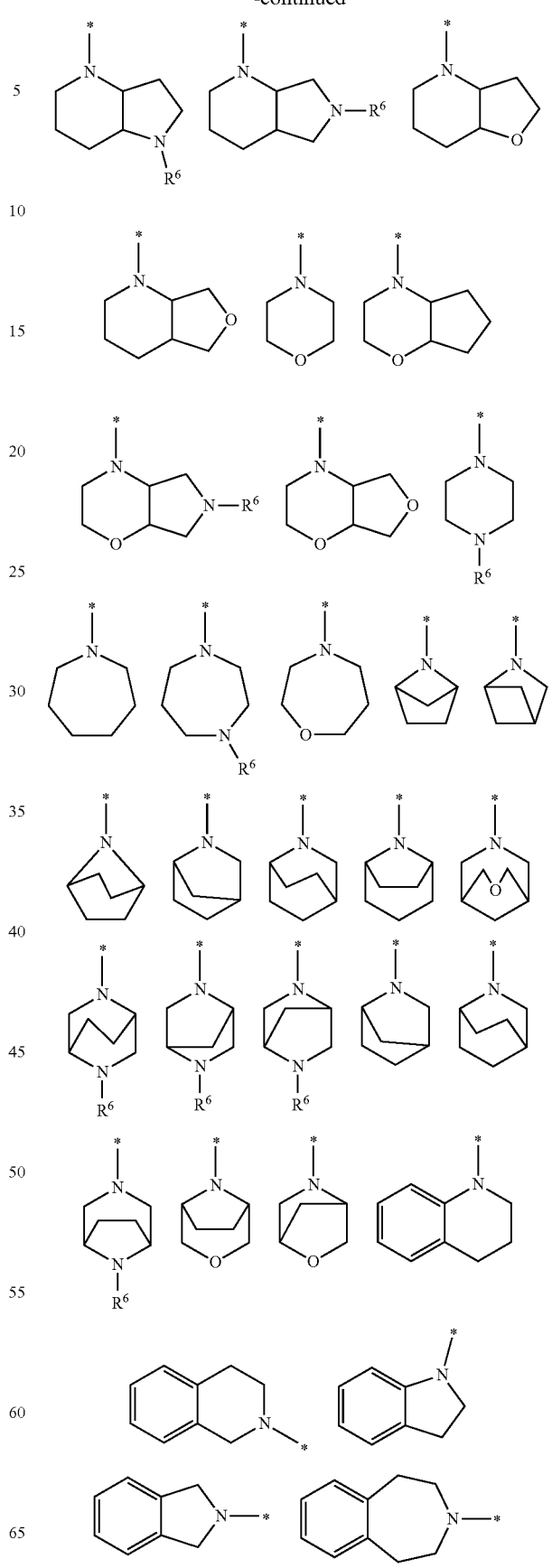

-continued

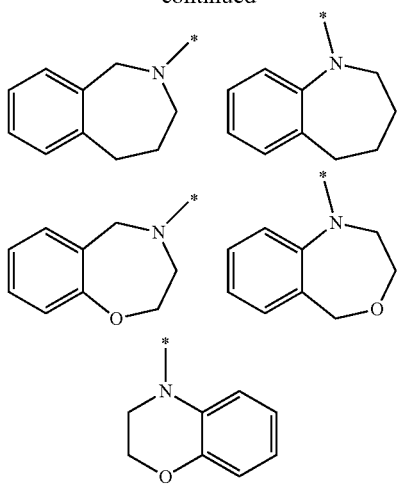

wherein 2 geminal hydrogen atoms of the above mentioned mono- or bicyclic ring may be replaced by a —(CH$_2$)$_{3-5}$— group and
wherein one —(CH$_2$)— group of the —(CH$_2$)$_{3-5}$— group may be replaced by —O— or —N(R$^6$)— and
wherein above mentioned mono- or bicyclic ring may optionally be substituted with 1 or 2 substituents independently selected from the group consisting of fluoro, phenyl, C$_{1-6}$-alkyl- which is optionally fluorinated with 1 to 13 fluorine atoms, azetidinyl, pyrrolidinyl, piperidinyl, azepanyl, oxetanyl, tetrahydrofuryl, tetrahydropyranyl, oxepanyl, dioxepanyl, tetrahydrothiophenyl, 1-oxo-tetrahydrothiophenyl 1,1-dioxo-tetrahydrothiophenyl, HO—, oxo, C$_{1-6}$-alkyl-O—, C$_{3-6}$-cycloalkyl-O—, HO—C$_{1-4}$-alkyl-, C$_{1-4}$-alkyl-O—C$_{1-4}$-alkyl-, oxetanyl-O—, tetrahydrofuryl-O—, tetrahydropyranyl-O— and (R$^6$)$_2$N—
wherein the aforementioned phenyl groups may optionally be substituted with 1 to 3 substituents independently selected from the group consisting of F$_3$C—, C$_{1-4}$-alkyl-O—, F$_3$CO—, F$_2$HCO—, FH$_2$CO—, cyano, halogen, and C$_{1-3}$-alkyl-,
R$^6$ is selected independently of each other from the group R$^{6b}$ consisting of
H, C$_{1-6}$-alkyl-, C$_{3-6}$-cycloalkyl, oxetanyl, tetrahydrofuryl, tetrahydropyranyl, pyridinyl, pyrimidinyl, pyridazinyl, pyrazinyl, triazinyl, thiazolyl, oxadiazolyl, oxazolyl, HC(O)—, C$_{1-6}$-alkyl-C(O)—, C$_{3-6}$-cycloalkyl-C(O)—, phenyl-C(O)—, C$_{1-4}$-alkyl-O—C(O)— and (C$_{1-4}$-alkyl)$_2$N—C(O)—,
wherein above mentioned C$_{1-6}$-alkyl-, C$_{3-6}$-cycloalkyl-, C$_{1-6}$-alkyl-C(O)— and C$_{3-6}$-cycloalkyl-C(O)— groups may optionally be substituted with 1-13 fluorine atoms and
wherein the aforementioned phenyl-C(O)—, pyridinyl, pyrimidinyl, pyridazinyl, pyrazinyl, triazinyl, thiazolyl oxadiazolyl and oxazolyl groups may optionally be substituted with 1 to 3 substituents independently selected from the group consisting of C$_{1-4}$-alkyl-O—, F$_3$C—, F$_3$CO—, F$_2$HCO—, FH$_2$CO—, cyano, halogen, and C$_{1-3}$-alkyl-,
R$^7$ is selected independently of each other from the group R$^{7b}$ consisting of H,
the tautomers thereof, the stereoisomers thereof, the mixtures thereof, and the alts thereof.

Further preferred are the following compounds listed in table 2:

| Ex. | Structure |
|---|---|
| 1 | 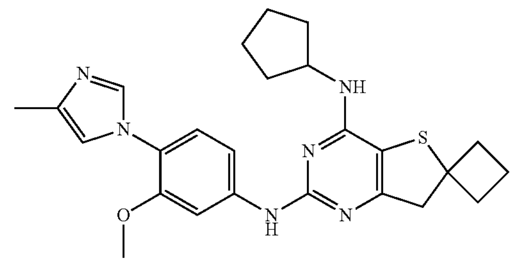 [SMILES: COc1cc(Nc2nc3c(c(NC4CCCC4)n2)SC2(CCC2)C3)ccc1-n1cnc(C)c1] |
| 2 | 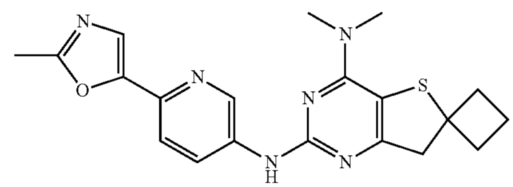 [SMILES: Cc1ncc(-c2ccc(Nc3nc4c(c(N(C)C)n3)SC3(CCC3)C4)cn2)o1] |
| 3 | 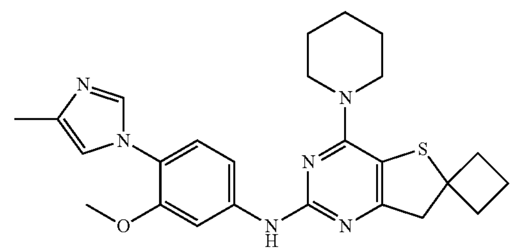 [SMILES: COc1cc(Nc2nc3c(c(N4CCCCC4)n2)SC2(CCC2)C3)ccc1-n1cnc(C)c1] |
| 4 | 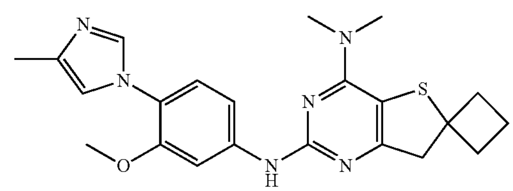 [SMILES: COc1cc(Nc2nc3c(c(N(C)C)n2)SC2(CCC2)C3)ccc1-n1cnc(C)c1] |
| 5 | 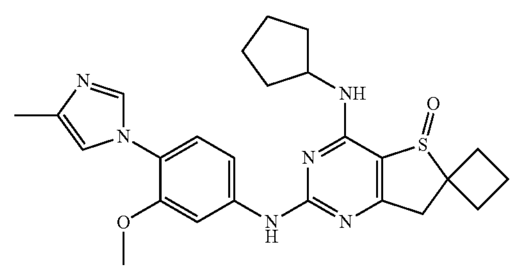 [SMILES: COc1cc(Nc2nc3c(c(NC4CCCC4)n2)S(=O)C2(CCC2)C3)ccc1-n1cnc(C)c1] |
| 6 | 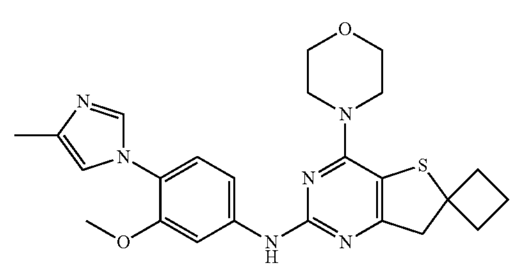 [SMILES: COc1cc(Nc2nc3c(c(N4CCOCC4)n2)SC2(CCC2)C3)ccc1-n1cnc(C)c1] |

-continued
| Ex. | Structure |
|---|---|
| 7 | 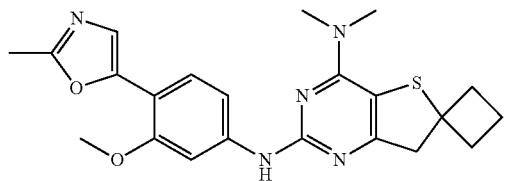 [SMILES: COc1cc(Nc2nc3c(c(N(C)C)n2)SC2(CCC2)C3)ccc1-c1cnc(C)o1] |
| 8 | 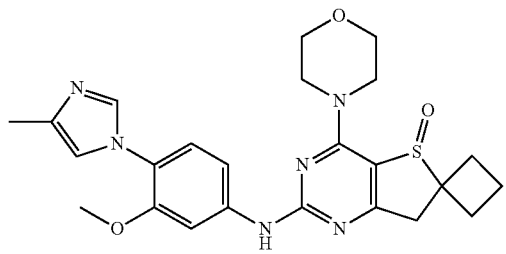 [SMILES: COc1cc(Nc2nc3c(c(N4CCOCC4)n2)S(=O)C2(CCC2)C3)ccc1-n1cnc(C)c1] |
| 9 | 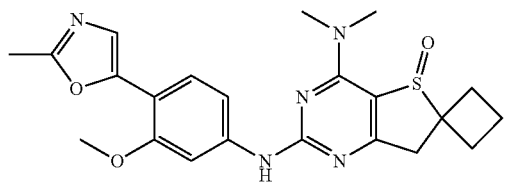 [SMILES: COc1cc(Nc2nc3c(c(N(C)C)n2)S(=O)C2(CCC2)C3)ccc1-c1cnc(C)o1] |
| 10 | 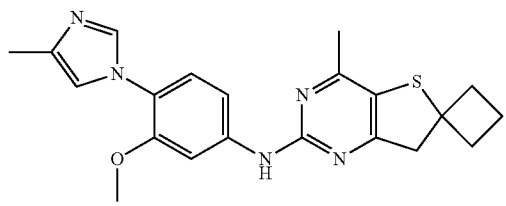 [SMILES: COc1cc(Nc2nc(C)c3c(n2)CC2(CCC2)S3)ccc1-n1cnc(C)c1] |
| 11 | 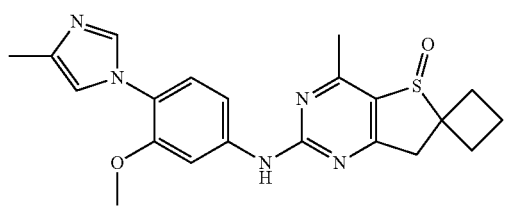 [SMILES: COc1cc(Nc2nc(C)c3c(n2)CC2(CCC2)S3=O)ccc1-n1cnc(C)c1] |
| 12 | 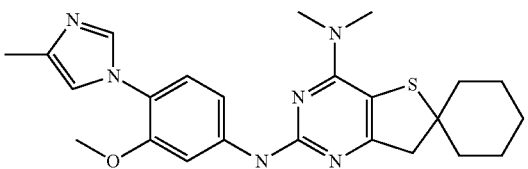 |
| 13 | 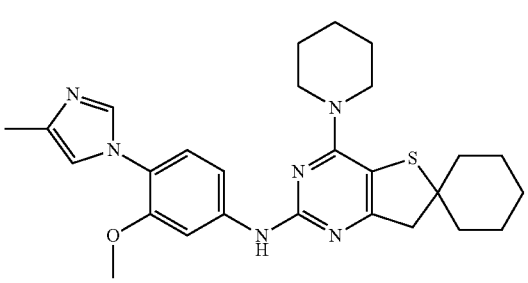 [SMILES: COc1cc(Nc2nc3c(c(N4CCCCC4)n2)SC2(CCCCC2)C3)ccc1-n1cnc(C)c1] |
-continued
| Ex. | Structure |
|---|---|
| 14 | 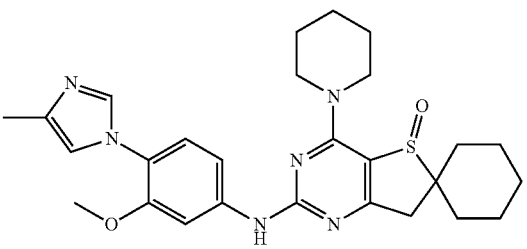 [SMILES: COc1cc(Nc2nc3c(c(N4CCCCC4)n2)S(=O)C2(CCCCC2)C3)ccc1-n1cnc(C)c1] |
| 15 | 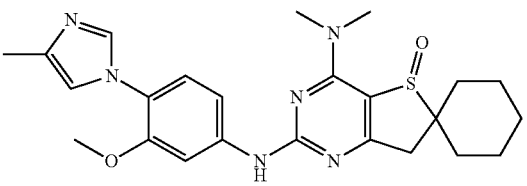 [SMILES: COc1cc(Nc2nc3c(c(N(C)C)n2)S(=O)C2(CCCCC2)C3)ccc1-n1cnc(C)c1] |
| 16 | 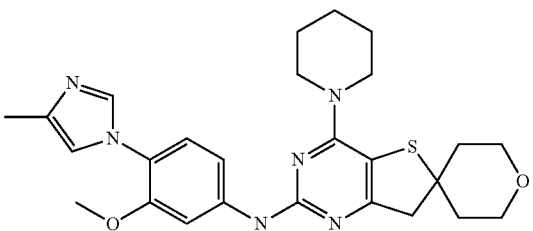 |
| 17 | 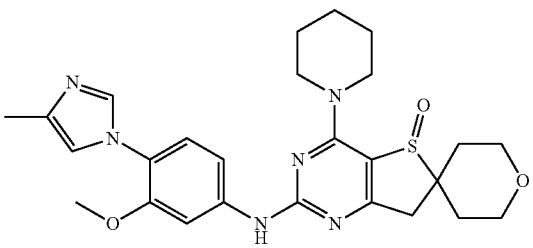 [SMILES: COc1cc(Nc2nc3c(c(N4CCCCC4)n2)S(=O)C2(CCOCC2)C3)ccc1-n1cnc(C)c1] |
| 18 | 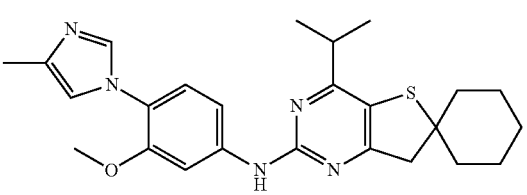 [SMILES: COc1cc(Nc2nc3c(c(C(C)C)n2)SC2(CCCCC2)C3)ccc1-n1cnc(C)c1] |
| 19 | 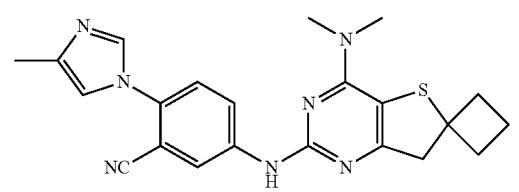 [SMILES: Cc1cn(-c2ccc(Nc3nc4c(c(N(C)C)n3)SC3(CCC3)C4)cc2C#N)cn1] |
| 20 | 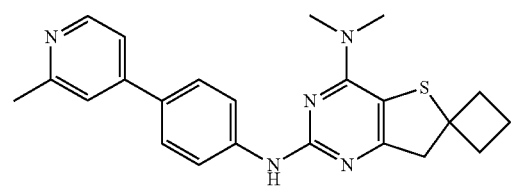 [SMILES: Cc1cc(-c2ccc(Nc3nc4c(c(N(C)C)n3)SC3(CCC3)C4)cc2)ccn1] |

| Ex. | Structure |
|---|---|
| 21 | 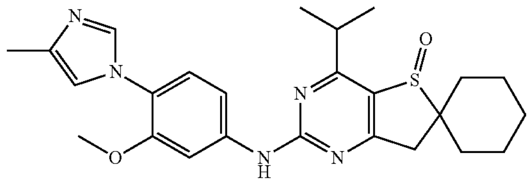 |
| 22 | 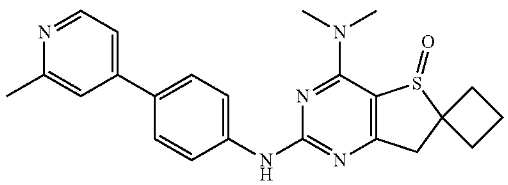 [SMILES: Cc1cc(-c2ccc(Nc3nc4c(c(N(C)C)n3)S(=O)C3(CCC3)C4)cc2)ccn1] |
| 23 | 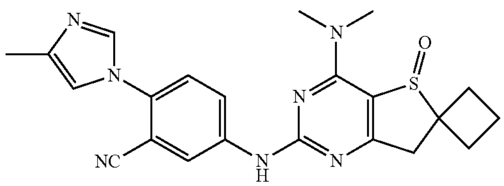 [SMILES: Cc1cn(-c2ccc(Nc3nc4c(c(N(C)C)n3)S(=O)C3(CCC3)C4)cc2C#N)cn1] |

Some terms used above and hereinafter to describe the compounds according to the invention will now be defined more closely.

Terms not specifically defined herein should be given the meanings that would be given to them by one of skill in the art in light of the disclosure and the context. As used in the specification, however, unless specified to the contrary, the following terms have the meaning indicated and the following conventions are adhered to. In the groups, radicals, or moieties defined below, the number of carbon atoms is often specified preceding the group, for example $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl group, the latter of which is bound to the core or to the group to which the substituent is attached.

In general, the attachment site of a given residue to another group shall be variable, i.e. any capable atom, bearing hydrogens to be replaced, within this residue may be the linking spot to the group being attached, unless otherwise indicated.

In case a compound of the present invention is depicted in form of a chemical name and as a formula in case of any discrepancy the formula shall prevail.

An asterisk may be used in sub-formulas to indicate the bond which is connected to the core molecule as defined.

The dotted lines in sub-formulas of substituent D indicate the spiro atom being part of the core structure of formula (I) and the substituent D. For example, the substructure

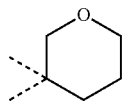

of substituent D means that ring D is attached to the core molecule of formula (I) via the indicated carbon atom resulting in the following structure:

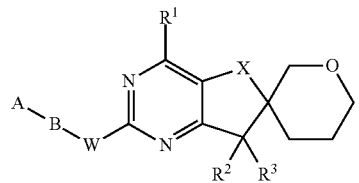

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include salts from ammonia, L-arginine, betaine, benethamine, benzathine, calcium hydroxide, choline, deanol, diethanolamine (2,2'-iminobis(ethanol)), diethylamine, 2-(diethylamino)-ethanol, 2-aminoethanol, ethylenediamine, N-ethyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, zinc hydroxide, acetic acid, 2,2-dichloro-acetic acid, adipic acid, alginic acid, ascorbic acid, L-aspartic acid, benzenesulfonic acid, benzoic acid, 2,5-dihydroxybenzoic acid, 4-acetamido-benzoic acid, (+)-camphoric acid, (+)-camphor-10-sulfonic acid, carbonic acid, cinnamic acid, citric acid, cyclamic acid, decanoic acid, dodecylsulfuric acid, ethane-1,2-disulfonic acid, ethanesulfonic acid, 2-hydroxy-ethanesulfonic acid, ethylenediaminetetraacetic acid, formic acid, fumaric acid, galactaric acid, gentisic acid, D-glucoheptonic acid, D-gluconic acid, D-glucuronic acid, glutamic acid, glutaric acid, 2-oxo-glutaric acid, glycerophosphoric acid, glycine, glycolic acid, hexanoic acid, hippuric acid, hydrobromic acid, hydrochloric acid, isobutyric acid, DL-lactic acid, lactobionic acid, lauric acid, lysine, maleic acid, (−)-L-malic acid, malonic acid, DL-mandelic acid, methanesulfonic acid, galactaric acid, naphthalene-1,5-disulfonic acid, naphthalene-2-sulfonic acid, 1-hydroxy-2-naphthoic acid, nicotinic acid, nitric acid, octanoic acid, oleic acid, orotic acid, oxalic acid, palmitic acid, pamoic acid (embonic acid), phosphoric acid, propionic acid, (−)-L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid. Further pharmaceutically acceptable salts can be formed with cations from metals like aluminium, calcium, lithium, magnesium, potassium, sodium, zinc and the like (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term "substituted" as used herein means that any one or more hydrogens on the designated atom is replaced with a selection from the indicated group, provided that the designated atom's viable valence number is not exceeded, and that the substitution results in a stable compound.

The term "partially unsaturated" as used herein means that in the designated group or moiety 1, 2, or more, preferably 1 or 2, double bonds are present. Preferably, as used herein, the term "partially unsaturated" does not cover fully unsaturated groups or moieties.

The term "C-linked heterocyclyl" as used herein means that the heterocyclyl group is connected to the core molecule according to formula I by a bond from a C-atom of the heterocyclyl ring.

The term "halogen" generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—CH_2—$, $H_3C—CH(CH_3)—CH_2—CH_2—$, $H_3C—CH_2—C(CH_3)_2—$, $H_3C—C(CH_3)_2—CH_2—$, $H_3C—CH(CH_3)—CH(CH_3)—$ and $H_3C—CH_2—CH(CH_2CH_3)—$, The term "$C_{2-n}$-alkenyl", is used for a group as defined in the definition for "$C_{1-n}$-alkyl" with at least two carbon atoms, if at least two of those carbon atoms of said group are bonded to each other by a double bond. The term $C_{2-5}$-alkenyl includes for example the radicals $H_2C=CH—$, $H_2C=CH—CH_2—$, $H_3C—CH=CH—$, $H_2C=CH—CH_2—CH_2—$, $H_3C—CH=CH—CH_2—$, $H_3C—CH_2—CH=CH—$, $(H_3C)_2C=CH—$, $H_2C=CH—CH_2—CH_2—CH_2—$, $H_3C—CH=CH—CH_2—CH_2—$, $H_3C—CH_2—CH=CH—CH_2—$, $H_3C—CH_2—CH_2—CH=CH—$, $H_2C=CH—CH=CH—CH_2—$ and $(H_3C)_2C=CH—CH_2—$.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. The term $C_{2-5}$-alkinyl includes for example the radicals $HC≡C—$, $HC≡C—CH_2—$, $H_3C—C≡C—$, $HC≡C—CH_2—CH_2—$, $H_3C—C≡C—CH_2—$, $H_3C—CH_2—C≡C—$, $HC≡C—CH_2—CH_2—CH_2—$, $H_3C—C≡C—CH_2—CH_2—$, $H_3C—CH_2—C≡C—CH_2—$, $H_3C—CH_2—CH_2—C≡C—$ and $(H_3C)_2CH—C≡C—$.

The term "carbocyclyl" as used either alone or in combination with another radical, means, if not mentioned otherwise, a mono- bi- or tricyclic ring structure consisting of 3 to 14 carbon atoms. The term, if not mentioned otherwise, refers to fully saturated, partially saturated and aromatic ring systems. The term "carbocycle" encompasses fused, bridged and spirocyclic systems.

Thus, the term "carbocyclyl" includes the following exemplary structures which are not depicted as radicals as each form may be attached through a covalent bond to any atom so long as appropriate valences are maintained:

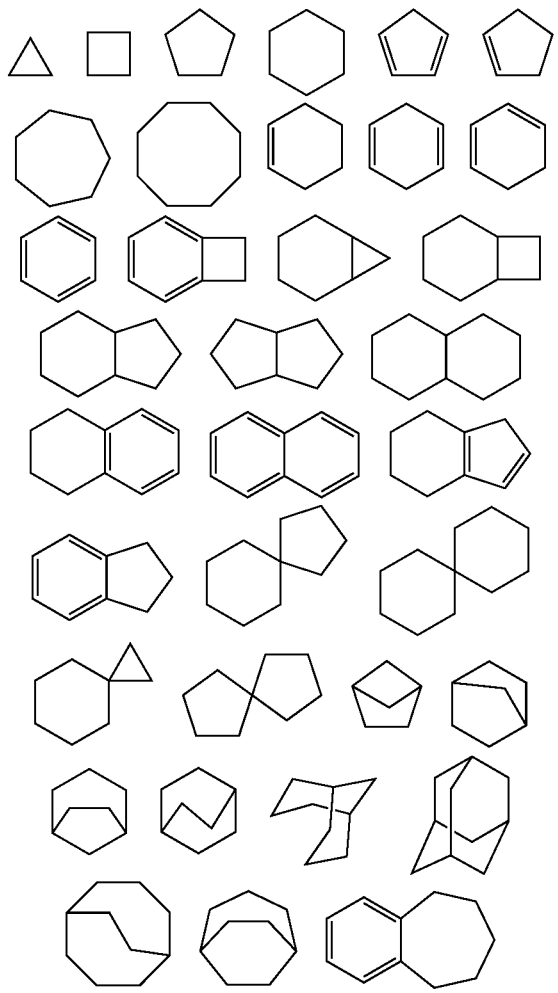

The term "$C_{3-n}$-cycloalkyl", wherein n is an integer from 4 to n, either alone or in combination with another radical denotes a cyclic, saturated, unbranched hydrocarbon radical with 3 to n C atoms. For example the term $C_{3-7}$-cycloalkyl includes cyclopropyl, cyclobutyl, cyclopentyl, cyclohexyl and cycloheptyl.

The term "heterocyclyl" means a saturated or unsaturated mono- or polycyclic-ring systems which may contain aromatic rings containing one or more heteroatoms selected from N, O or $S(O)_r$, wherein r=0, 1 or 2, consisting of, if not mentioned otherwise, 3 to 14 ring atoms wherein none of the heteroatoms is part of an aromatic ring. The term "heterocycle" is intended to include all the possible isomeric forms.

Thus, the term "heterocyclyl" includes the following exemplary structures which are not depicted as radicals as each form may be attached through a covalent bond to any atom so long as appropriate valences are maintained:

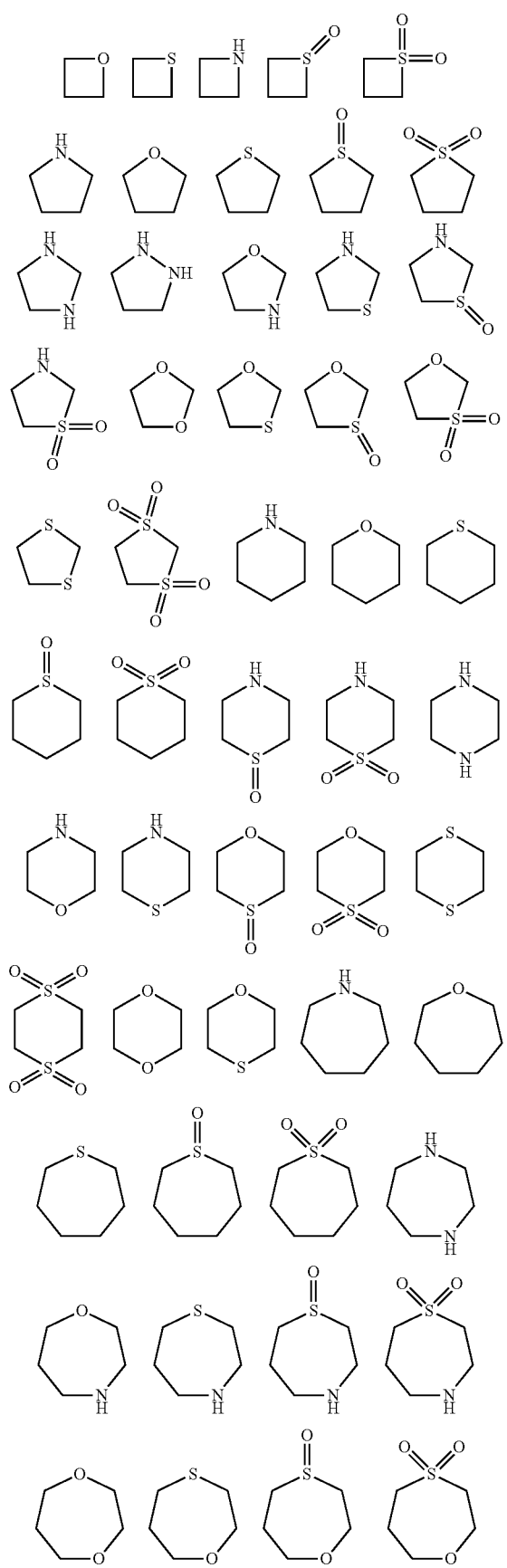
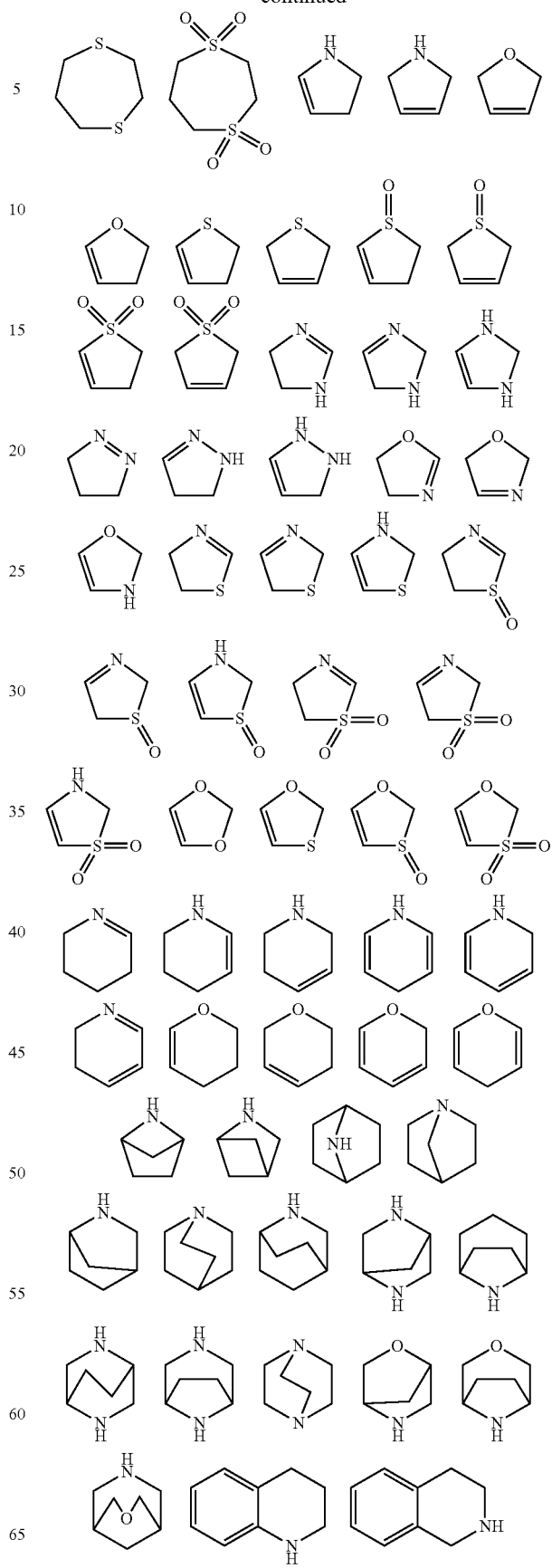
-continued

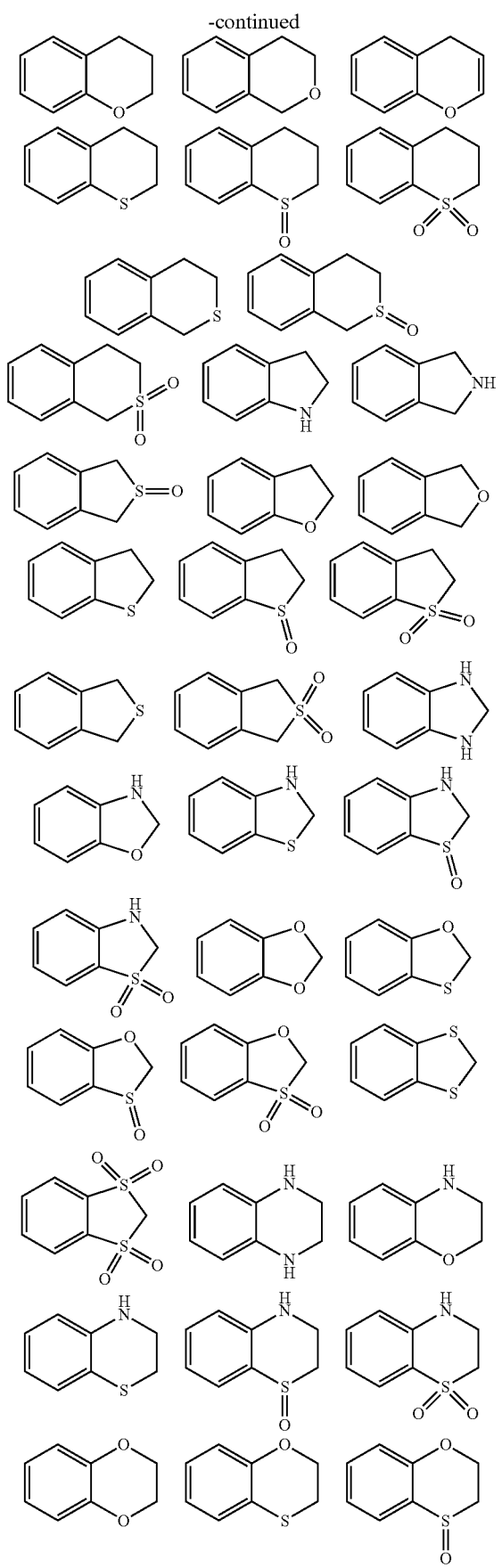
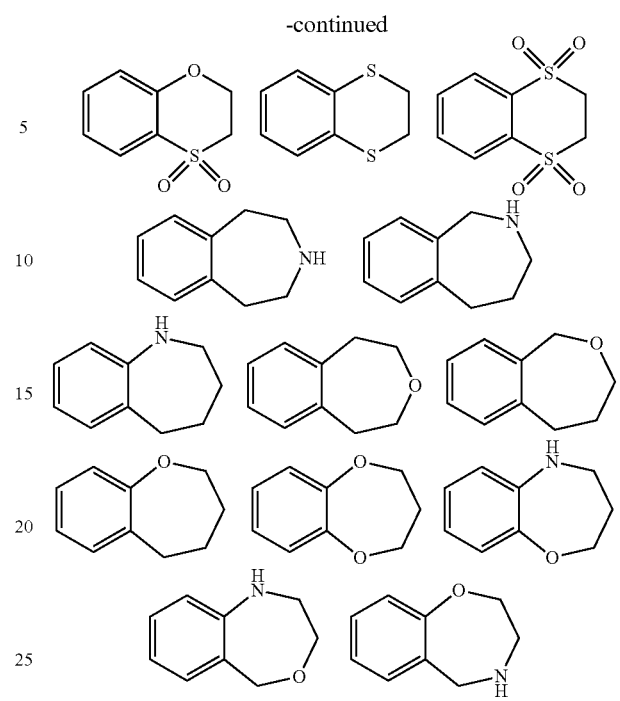

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means a mono- or polycyclic-ring systems containing one or more heteroatoms selected from N, O or $S(O)_r$, wherein r=0, 1 or 2, consisting of 5 to 14 ring atoms wherein at least one of the heteroatoms is part of aromatic ring. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

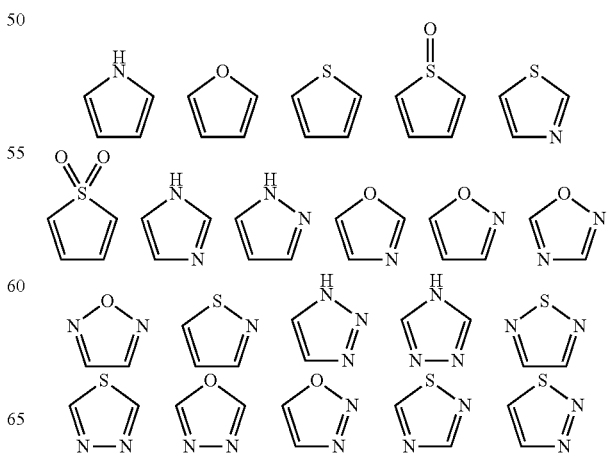

Many of the terms given above may be used repeatedly in the definition of a formula or group and in each case have one of the meanings given above, independently of one another.

The compounds according to the invention may be obtained using methods of synthesis known in principle. Preferably, the compounds are obtained by the following methods according to the invention which are described in more detail hereinafter.

The following schemes shall illustrate a process to manufacture the compounds of the present invention by way of example:

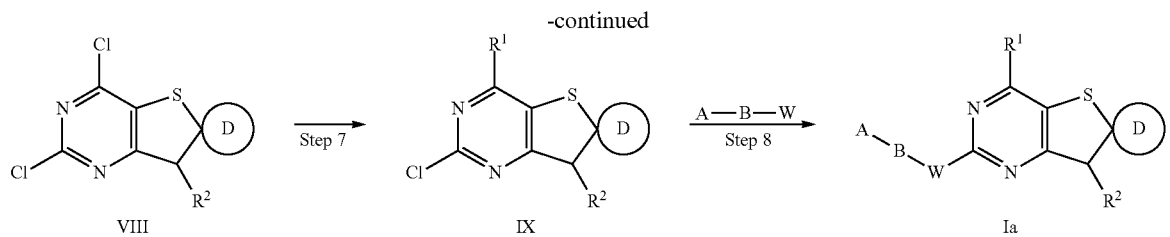

Scheme 1: In a first step a cyclic ketone (II) is condensed with an $R^2$-substituted acetic acid ester by heating the reactants in an appropriate solvent like ethanol in the presence of a base (e.g. piperidine) to form substituted acrylic ester derivative (III). These compounds are converted in a second step to the corresponding sulfur adducts (IV) in a Michael-type reaction by treatment with a mercapto acetic acid ester in presence of a base (e.g. piperidine). In a third step, heating under basic conditions (e.g. in an ethanolic solution of sodium ethanolate), leads to the corresponding Dieckmann beta-keto esters (V). In a fourth step, heating with 2-ethyl-isothiourea in an appropriate solvent (e.g. ethanol or isopropanol), results in the formation of 6,7-dihydro-thieno[3,2-d]pyrimidin-4-oles (VI). These compounds are hydrolysed in a fifth step in aqueous hydrochloric acid under heating to give the corresponding thieno pyrimidine diols (VII). Heating of the pyrimidine diols (VII) in an appropriate chlorinating agent (e.g. phosphorous oxychloride, phosphorous pentachloride) forms in a sixth step the corresponding dichlorides (VIII). In a seventh step, these dichlorides are converted into compounds (IX). In case $R^1$ represents a nitrogen radical, an amine is heated with dichloride (VIII) to give the corresponding product (IX).

In case $R^1$ represents a carbon radical, the dichloride compound (VIII) may be reacted with a suitable carbon nucleophile (e.g. an alkyl magnesium grignard reagent) in the presence of a suitable metal catalyst (e.g. Fe(acac)$_3$ or palladium (0) tetrakis triphenyl phosphine) in a solvent such as tetrahydrofurane or the like to give the corresponding carbon substituted products (IX).

These chloro pyrimidines (IX) are converted in an eighth step into the final products (Ia): chloro pyrimidines (IX) are heated with an amine A-B-W in the presence of a suitable catalyst (e.g. Pd(OAc)$_2$ or Pd$_2$(dba)$_3$), a ligand (e.g. BINAP, dppf or Xantphos) and a base (e.g. cesium carbonate or potassium tert.-butoxide) in a suitable solvent like tetrahydrofurane, 1,4-dioxane or the like to form the final amino substituted 6,7-dihydro-thieno[3,2-d]pyrimidines (Ia).

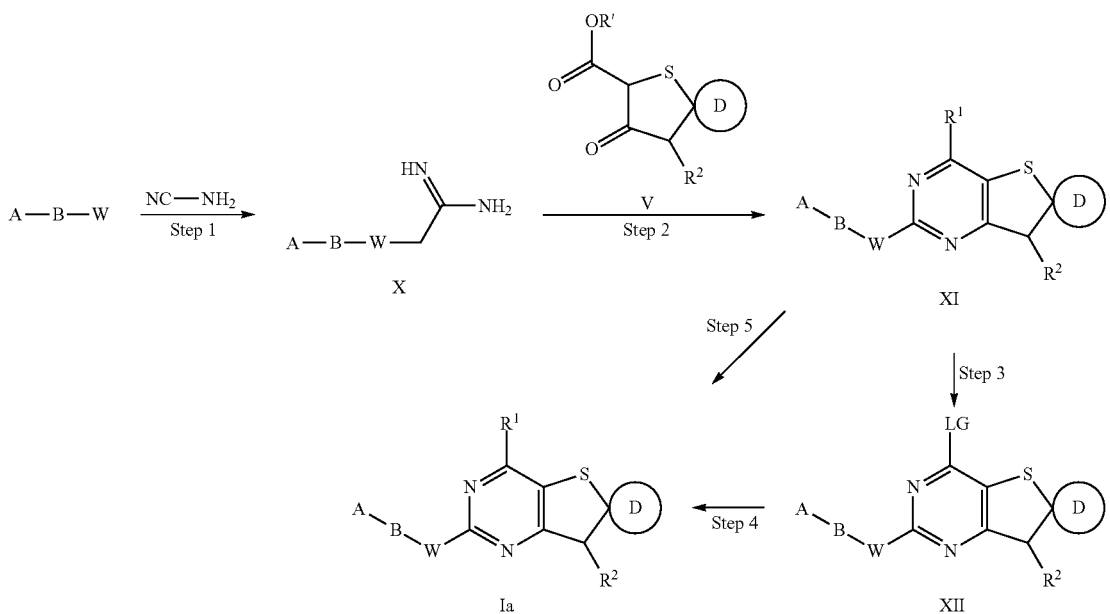

Scheme 2: In a first step an amine A-B-W is heated with cyanamide in hydrochloric acid to give a guanidine (X). Guanidines (X) are condensed with beta-keto ester (V) in a second step by heating the reactants in an appropriate solvent like ethanol or pyridine to form dihydrothieno pyrimidine (XI). In a third step the hydroxy group of dihydrothieno pyrimidines (XI) is transformed into a leaving group such as CF$_3$SO$_2$—O— or halogen to give the corresponding dihydrothieno pyrimidines (XII). Sulfonylation can be achieved with triflate anhydride or bis(trifluoromethylsulfonyl)-phenylimid in the presence of base (such as DBU or triethylamine). Chlorination can be achieved by heating the hydroxy pyrimidine (XI) in a suitable chlorination agent such as phosphorous oxy chloride. In a fourth step, these activated dihydrothieno pyrimidines (XII) are converted into final compounds (Ia). In case $R^1$ represents a nitrogen radical, an amine is heated with compound (XII) in a solvent like tetrahydrofurane, 1,4-dioxane or the like to give the corresponding final product (Ia).

In case $R^1$ represents a carbon radical, compound (XII) may be reacted with a suitable carbon nucleophile (e.g. an alkyl or aryl magnesium grignard reagent) in the presence of a suitable catalyst (e.g. $Fe(acac)_3$ or palladium(0) tetrakis triphenyl phosphine) in a solvent such as tetrahydrofurane or the like to give the corresponding carbon substituted final products (Ia).

In case $R^1$ represents an oxygen radical, compound (XI) may be converted in a fifth step into an ether compound of formula (I) using the "Mitsunobu" method (see for examples *Tet. Lett.* 1994, 35, 2819 or *Synlett* 2005, 18, 2808). Trialkyl or triaryl phosphine (such as tributyl phosphine or triphenyl phosphine) and a suitable dialkyl azadicarboxylate (e.g. DIAD, DEAD) are added to a compound of general formula (XI) in the presence of an appropriate alcohol in a suitable solvent (e.g. THF) to give ether of the general formula (Ia).

The compounds according to the invention are advantageously also obtainable using the methods described in the examples that follow, which may also be combined for this purpose with methods known to the skilled man from the literature.

As already mentioned, the compounds of general formula I according to the invention and the physiologically acceptable salts thereof have valuable pharmacological properties, particularly as modulators of γ-secretase.

Biological Examples

Screening for compounds which preferentially inhibit production of Aβ42 vs. total Aβ was performed using H4 neuroglioma cells stably expressing the human APP695 isoform grown in Dulbecco's Modified Eagles medium (DMEM) GlutaMAX supplemented with 10% Fetal Bovine Serum and 250 μg/mL Zeocine. Cells were plated out to near confluency. The compounds to be tested were received as 10 mM stocks in 100% DMSO. A dilution series was initially generated in 100% DMSO and then diluted 200-fold in cell culture media such that the tested concentration range was 30 μM to 0.1 nM and the final DMSO concentration was 0.5%. The diluted compounds were incubated with the cells for 22 hours in an incubator at 37° C. and 5% $CO_2$. Aβ42 as well as Aβ total levels were then measured post-incubation from the supernatant of the cells. Aβ42 levels were determined using a specific electrochemiluminescence assay provided by Meso Scale Discovery (Catalog #L21CA-1) according to the manufacturer's protocol. Aβ total levels were likewise determined using a specific electrochemiluminescence assay provided by Meso Scale Discovery (Catalog #L21ZA-1) according to the manufacturer's protocol. To identify compounds which preferentially inhibited Aβ42, the ratio Aβ total $IC_{50}$/Aβ42 $IC_{50}$ was determined, where the higher the ratio, the more specific the inhibition of Aβ42 over Aβ total.

The compounds of general formula I according to the invention for example have $IC_{50}$ values below 30000 nM, particularly below 1000 nM, most preferably below 500 nM.

TABLE 3

Activity of the examples (Ex) compiled in the experimental part, based on $Aβ_{42}$ cellular $IC_{50}$ values in H4 neuroglioma cells (see above).

| Ex | $IC_{50}$ [μM] | Ratio Aβ(total)/$Aβ_{42}$ |
|---|---|---|
| 1 | 0.19 | 37 |
| 2 | 0.52 | 51 |
| 3 | 0.09 | 85 |
| 4 | 0.13 | 50 |
| 5 | 0.22 | 54 |
| 6 | 0.14 | 55 |
| 7 | 0.10 | 242 |
| 8 | 3.25 | >9 |
| 9 | 0.16 | >182 |
| 10 | 0.13 | 110 |
| 11 | 1.55 | 19 |
| 12 | 0.12 | 61 |
| 13 | 0.13 | 57 |
| 14 | 0.12 | 100 |
| 15 | 0.30 | 61 |
| 16 | 0.82 | >36 |
| 17 | 0.53 | 51 |
| 18 | 7.59 | 2 |
| 19 | 0.37 | 55 |
| 20 | 1.38 | 8 |
| 21 | 19.70 | 1 |
| 22 | 0.77 | 12 |
| 23 | 1.19 | 25 |

Whereas γ-Secretase inhibitors simultaneously inhibit production of all Aβ species, γ-Secretase modulators preferentially inhibit the production of the neurotoxic Aβ42 species. In order to absolutely define the described compounds as modulators of γ-Secretase as opposed to simply inhibitors of γ-Secretase, measurements of not only Aβ42 but also Aβ total are performed. When the ratio of Aβ total $IC_{50}$/Aβ42 $IC_{50}$ is >1, the compound preferentially inhibits Aβ42 production, thereby demonstrating that the compound is in fact a γ-Secretase modulator.

In view of their ability to modulate the activity of γ-secretase, the compounds of general formula I according to the invention are suitable for the treatment and/or preventative treatment of all those conditions or diseases which may be affected by the formation of Aβ peptides. Therefore, compounds according to the invention are particularly suitable for the prevention or treatment of diseases, particularly Down's syndrome, Abeta-amyloid angiopathy, cerebral amyloid angiopathy, hereditary cerebral hemorrhage, a disorder associated with cognitive impairment, MCI ("mild cognitive impairment"), Alzheimer's Disease, memory loss, attention deficit symptoms associated with Alzheimer's disease, neurodegeneration associated with Alzheimer's disease, diffuse Lewy body type of Alzheimer's Disease, dementia of mixed vascular origin, dementia of degenerative origin, pre-senile dementia, senile dementia, dementia associated with Parkinson's disease, progressive supranuclear palsy or cortical basal degeneration, the dry form of age-related macular degeneration and glaucoma.

Preferably the compounds according to the invention, including the physiologically acceptable salts thereof, are suitable for the prevention or treatment of Alzheimer's Disease, the dry form of age-related macular degeneration and/or MCI.

In particular, the compounds according to the invention, including the physiologically acceptable salts thereof, are suitable for the prevention or treatment of Alzheimer's Disease and/or MCI.

In a further aspect of the present invention the present invention relates to methods for the treatment or prevention of above mentioned diseases and conditions, which method comprises the administration of an effective amount of a compound of general formula I to a human being.

The dose range of the compounds of general formula I applicable per day is usually from 0.1 to 1000 mg, preferably from 1 to 500 mg by oral route, in each case administered 1 to 4 times a day.

Each dosage unit may conveniently contain from 0.1 to 500 mg, preferably 1 to 100 mg.

The actual pharmaceutically effective amount or therapeutic dosage will of course depend on factors known by those skilled in the art such as age and weight of the patient, route of administration and severity of disease. In any case the combination will be administered at dosages and in a manner which allows a pharmaceutically effective amount to be delivered based upon patient's unique condition.

Suitable preparations for administering the compounds of formula I will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) should be in the range from 0.1 to 95 wt.-%, preferably 5.0 to 90 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers.

For this purpose, the compounds of formula I prepared according to the invention may be formulated, optionally together with other active substances, together with one or more inert conventional carriers and/or diluents, e.g. with corn starch, lactose, glucose, microcrystalline cellulose, magnesium stearate, citric acid, tartaric acid, water, polyvinylpyrrolidone, water/ethanol, water/glycerol, water/sorbitol, water/polyethylene glycol, propylene glycol, cetylstearyl alcohol, carboxymethylcellulose or fatty substances such as hard fat or suitable mixtures thereof.

The compounds according to the invention may also be used in conjunction with other active substances, particularly for the treatment and/or prevention of the diseases and conditions mentioned above. Other active substances which are suitable for such combinations include, for example, BACE inhibitors; amyloid aggregation inhibitors (e.g. ELND-005); directly or indirectly acting neuroprotective and/or disease-modifying substances; anti-oxidants (e.g. vitamin E or ginkolide); anti-inflammatory substances (e.g. Cox inhibitors, NSAIDs additionally or exclusively having Abeta lowering properties); HMG-CoA reductase inhibitors (statins); acetylcholinesterase inhibitors (e.g., donepezil, rivastigmine, tacrine, galantamine); NMDA receptor antagonists (e.g. memantine); AMPA receptor agonists; AMPA receptor positive modulators, AMPAkines, monoamine receptor reuptake inhibitors, substances modulating the concentration or release of neurotransmitters; substances inducing the secretion of growth hormone (e.g., ibutamoren mesylate and capromorelin); CB-1 receptor antagonists or inverse agonists; antibiotics (e.g., minocyclin or rifampicin); PDE2, PDE4, PDE5, PDE9, PDE10 inhibitors, GABAA receptor inverse agonists, GABAA receptor antagonists, nicotinic receptor agonists or partial agonists or positive modulators, alpha4beta2 nicotinic receptor agonists or partial agonists or positive modulators, alpha7 nicotinic receptor agonists or partial agonists or positive modulators; histamine H3 antagonists, 5 HT-4 agonists or partial agonists, 5HT-6 antagonists, alpha2-adrenoreceptor antagonists, calcium antagonists, muscarinic receptor M1 agonists or partial agonists or positive modulators, muscarinic receptor M2 antagonists, muscarinic receptor M4 antagonists, metabotropic glutamate-receptor 5 positive modulators, glycine transporter 1 inhibitors, antidepressants, such as citalopram, fluoxetine, paroxetine, sertraline and trazodone; anxiolytics, such as lorazepam and oxazepam; antiphychotics, such as aripiprazole, clozapine, haloperidol, olanzapine, quetiapine, risperidone and ziprasidone, and other substances that modulate receptors or enzymes in a manner such that the efficacy and/or safety of the compounds according to the invention is increased and/or unwanted side effects are reduced. The compounds according to the invention may also be used in combination with immunotherapies (e.g., active immunisation with Abeta or parts thereof or passive immunisation with humanised anti-Abeta antibodies or nanobodies) for the treatment of the above-mentioned diseases and conditions.

The dosage for the combination partners mentioned above is usefully ⅕ of the lowest dose normally recommended up to 1/1 of the normally recommended dose.

Therefore, in another aspect, this invention relates to the use of a compound according to the invention or a physiologically acceptable salt thereof combined with at least one of the active substances described above as a combination partner, for preparing a pharmaceutical composition which is suitable for the treatment or prevention of diseases or conditions which can be affected by modulation of γ-secretase. These are preferably Aβ-related pathologies, particularly one of the diseases or conditions listed above, most particularly Alzheimer's Disease and/or MCI.

The use of the compound according to the invention, or a physiologically acceptable salt thereof, in combination with another active substance may take place simultaneously or at staggered times, but particularly within a short space of time. If they are administered simultaneously, the two active substances are given to the patient together; while if they are used at staggered times the two active substances are given to the patient within a period of less than or equal to 12 hours, but particularly less than or equal to 6 hours.

Consequently, in another aspect, this invention relates to a pharmaceutical composition which comprises a compound according to the invention or a physiologically acceptable salt of such a compound and at least one of the active substances described above as combination partners, optionally together with one or more inert carriers and/or diluents.

The compound according to the invention, or a physiologically acceptable salt thereof, and the additional active substance to be combined therewith may both be present together in one formulation, for example a tablet or capsule, or separately in two identical or different formulations, for example as a so-called kit-of-parts.

EXAMPLES

The following examples are intended to illustrate the invention, without restricting its scope.

As a rule, $^1$H-NMR and/or mass spectra have been obtained for the compounds prepared. Unless otherwise stated, Rf values were obtained using ready-made silica gel 60 F254 TLC plates (E. Merck, Darmstadt, item no. 1.05714) without chamber saturation. The ratios given for the eluants refer to units by volume of the solvents in question. Chromatographic purification was done using silica gel supplied by E. Merck, Darmstadt (Silica gel 60, 0.040-0.063 mm, item no. 1.09385.2500). If the configuration is not specified in detail, it is unclear whether the compound is a pure stereoisomer or a mixture of enantiomer and diastereomer.

The following abbreviations are used in the test descriptions:
aq. aqueous
CH Cyclohexane
DAD Diode array detection
DBU 1,8-Diazabicyclo[5.4.0]undec-7-ene
DCM Dichloromethane
DEAD Diethyl azodicarboxylate
DIAD Diisopropyl azodicarboxylate
DIPEA N-Ethyl-diisopropylamine
DMSO Dimethylsulphoxide
DMF N,N-Dimethylformamide
sat. saturated
h Hour(s)
HPLC High performance liquid chromatography
M Molar
MeOH Methanol
min Minute(s)
mL Milliliters
µL Microliters
mmol Millimoles
µmol Micromoles
MPLC Medium pressure liquid chromatography
NMP N-Methyl-pyrrolidinone
PE Petrol ether
Rf Retention factor
Rt Retention time
tert. tertiary
TEA Triethylamine
TFA Trifluoroacetic acid
THF Tetrahydrofurane
UPLC Ultra performance liquid chromatography All references to brine refer to a saturated aqueous solution of sodium chloride. Unless otherwise indicated, all temperatures are expressed in ° C. (degrees Centigrade). All reactions are conducted not under an inert atmosphere at room temperature unless otherwise noted.

HPLC/UPLC Methods:

Method A:

| Device: Water Acquity UPLC, Waters Acquity SQ detector and Waters Acquity PDA detector Column: Waters XBridge C18, 2.1 × 20 mm, 2.5 µm | | | | |
|---|---|---|---|---|
| Time [min] | % Solvent A [H$_2$O, 0.10% TFA] | % Solvent B [Methanol] | Flow rate [ml/min] | Temperature [° C.] |
| 0.0 | 95 | 5 | 1.4 | 60 |
| 0.05 | 95 | 5 | 1.4 | 60 |
| 1.00 | 0 | 100 | 1.4 | 60 |
| 1.1 | 0 | 100 | 1.4 | 60 |

Method B:

| Device: Water Acquity UPLC, Waters Acquity SQ detector and Waters Acquity PDA detector Column: Waters Sunfire C18, 2.1 × 20 mm, 2.5 µm | | | | |
|---|---|---|---|---|
| Time [min] | % Solvent A [H$_2$O, 0.10% TFA] | % Solvent B [Methanol] | Flow rate [ml/min] | Temperature [° C.] |
| 0.00 | 99 | 1 | 1.3 | 60 |
| 0.15 | 99 | 1 | 1.3 | 60 |
| 1.10 | 0 | 100 | 1.3 | 60 |
| 1.25 | 0 | 100 | 1.3 | 60 |

Method C:

| Device: Waters Alliance HPLC, Waters Alliance ZQ detector and Waters Alliance PDA detector Column: Waters SunFire C18, 4.6 × 30 mm, 3.5 µm | | | | |
|---|---|---|---|---|
| Time [min] | % Solvent A [H$_2$O, 0.10% TFA] | % Solvent B [Methanol] | Flow rate [ml/min] | Temperature [° C.] |
| 0.0 | 95 | 5 | 4 | 60 |
| 1.6 | 0 | 100 | 4 | 60 |
| 1.85 | 0 | 100 | 4 | 60 |
| 1.9 | 95 | 5 | 4 | 60 |

Example 1

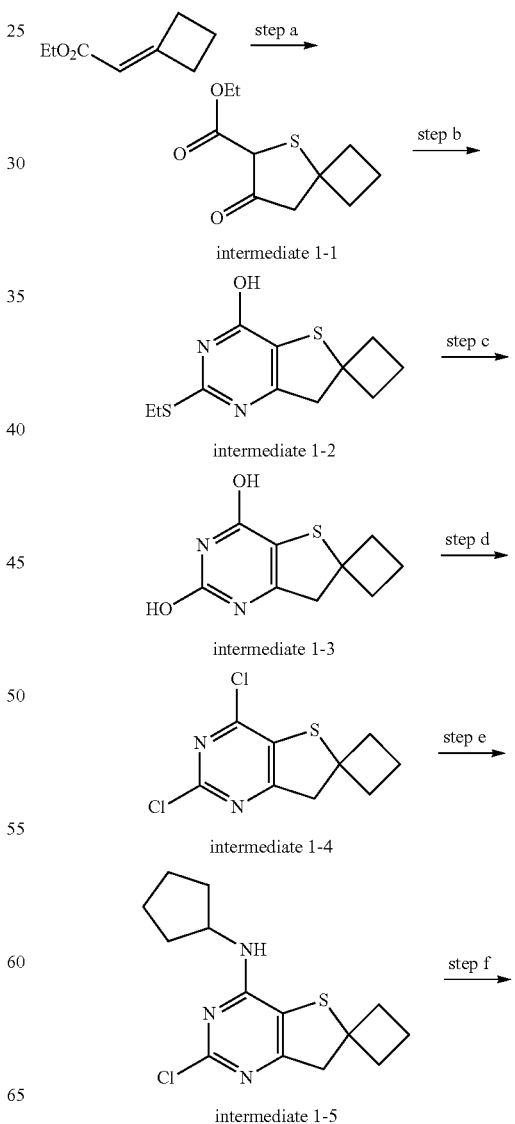

-continued

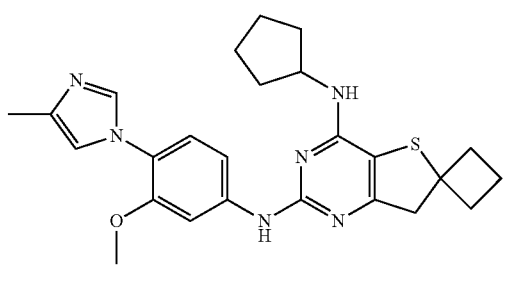

example 1

Step a

Intermediate 1-1

7.4 mL (64.2 mmol) Mercapto acetic acid ethyl ester and 0.6 mL (6.4 mmol) piperidine are mixed together in ethanol (113 mL). After addition of 9.0 g cyclobutyliden acetic acid ethyl ester (64.2 mmol) the mixture is stirred for 20 h. A total of 2.7 g (115.6 mmol) sodium metal is added carefully in portions. After complete addition the reaction mixture is heated to reflux for one hour and then left to stir for 5 days. After cooling to 0-5° C. 8.4 mL (144.5 mmol) acetic acid is added carefully. Then the reaction mixture is concentrated in vacuo to give crude product that is purified by MPLC (silica gel, CH/Ethyl acetate 9:1).

$C_{10}H_{14}O_3S$ (214.28)

Mass spectrometry (ESI$^+$): m/z=215 [M+H]$^+$

HPLC (Method A): Retention time=0.62 min.

Step b

Intermediate 1-2

5.0 g (27.0 mmol) S-Ethyl thiourea hydrobromide and 4.2 g (30.3 mmol) potassium carbonate are mixed together in water (30 mL) followed by addition of 5.0 g (15.2 mmol) 7-oxo-5-thia-spiro[3.4]octane-6-carboxylic acid ethyl ester (intermediate 1-1). After sonication for 3 h the reaction mixture is diluted with ethyl acetate. The organic phase is washed with brine, dried over sodium sulphate and concentrated in vacuo. The crude product is purified by MPLC (silica gel, CH/Ethyl acetate gradients 9:1→1:9).

$C_{11}H_{14}N_2OS_2$ (254.37)

Mass spectrometry (ESI$^+$): m/z=255 [M+H]$^+$

HPLC (Method A): Retention time=0.68 min.

Step c

Intermediate 1-3

300.0 mg (1.2 mmol) of intermediate 1-2 are suspended in aqueous hydrochloric acid solution (4N, 4.1 mL) and heated with microwave irradiation for 60 min at 130° C. After cooling the mixture is directly freeze-dried to obtain the product.

$C_9H_{10}N_2O_2S$ (210.25)

Mass spectrometry (ESI$^+$): m/z=211 [M+H]$^+$

HPLC (Method A): Retention time=0.38 min.

Step d

Intermediate 1-4

240.0 mg (1.1 mmol) of intermediate 1 to 3 are suspended in 4.3 mL (46.0 mmol) phosphorous oxy chloride and heated with microwave irradiation for 30 min at 145° C. After cooling the mixture is poured onto ice water and extracted with DCM. The organic phase is separated and concentrated in vacuo to give the crude product.

$C_9H_8Cl_2N_2S$ (247.14)

Mass spectrometry (ESI$^+$): m/z=247 [M+H]$^+$

HPLC (Method A): Retention time=0.79 min.

Step e

Intermediate 1-5

61.8 mg (250.0 µmol) of intermediate 1-4, 27.2 µL (275.0 µmol) cyclopentyl amine and 152.5 µL (875.0 µmol) DIPEA are mixed in 0.5 mL DMSO and are stirred for 2 h.

Another 27.2 µL of cyclopentyl amine is added and stirred is continued for another hour. The mixture is purified directly by HPLC to obtain the product.

$C_{14}H_{18}ClN_3S$ (295.83)

Mass spectrometry (ESI$^+$): m/z=296 [M+H]$^+$

HPLC (Method A): Retention time=0.82 min.

Step f

Example 1

44.0 mg (149.0 µmol) of intermediate 1-5, 39.3 mg (193.0 µmol) 3-methoxy-4-(4-methyl-imidazol-1-yl)-phenylamine, 34.6 mg (268.0 µmol) cesium carbonate, 3.3 mg (15.0 µmol) palladium(II) acetate and 17.2 mg (30.0 µmol) Xantphos are mixed together in 2 mL 1,4-dioxane. The reaction is heated by microwave irradiation for 6 h at 120° C. After cooling the mixture is diluted with methanol and purified directly by HPLC to give the title compound as TFA salt.

$C_{25}H_{30}N_6OS$ (462.62)

Mass spectrometry (ESI$^+$): m/z=463 [M+H]$^+$

HPLC (Method B): Retention time=0.72 min.

In analogy to the preparation of example 1 the following compounds are obtained:

| Nr. | Structure | Mass signal(s) | $R_f$ Value or $R_t$ |
|---|---|---|---|
| 2 | 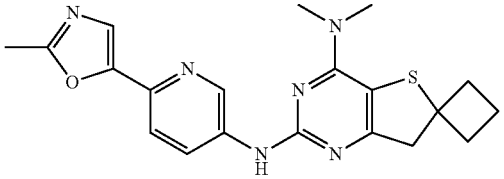 [SMILES: Cc1ncc(-c2ccc(Nc3nc4c(c(N(C)C)n3)SC3(CCC3)C4)cn2)o1] Obtained as TFA salt | $(M + H)^+ = 395$ | 0.79 min (method B) |
| 3 | 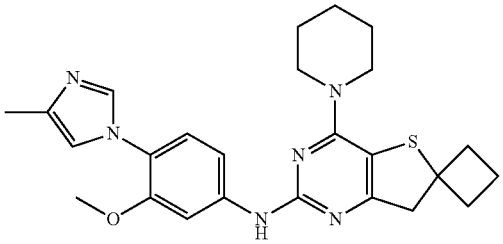 [SMILES: COc1cc(Nc2nc3c(c(N4CCCCC4)n2)SC2(CCC2)C3)ccc1-n1cnc(C)c1] Obtained as TFA salt | $(M + H)^+ = 463$ | 0.75 min (method B) |
| 4 | 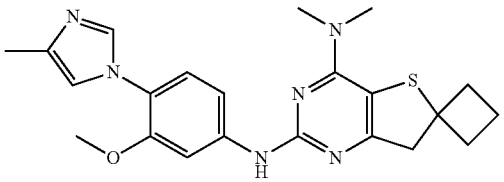 [SMILES: COc1cc(Nc2nc3c(c(N(C)C)n2)SC2(CCC2)C3)ccc1-n1cnc(C)c1] Obtained as TFA salt | $(M + H)^+ = 423$ | 0.68 min (method B) |
| 6 | 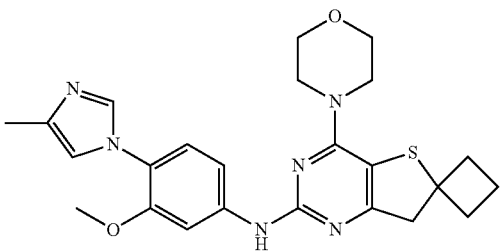 [SMILES: COc1cc(Nc2nc3c(c(N4CCOCC4)n2)SC2(CCC2)C3)ccc1-n1cnc(C)c1] Obtained as TFA salt | $(M + H)^+ = 465$ | 0.62 min (method A) |
| 7 | 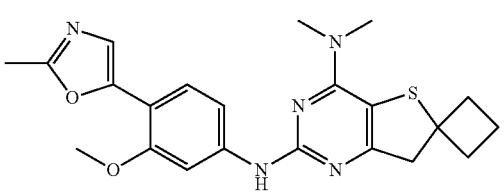 [SMILES: COc1cc(Nc2nc3c(c(N(C)C)n2)SC2(CCC2)C3)ccc1-c1cnc(C)o1] Obtained as TFA salt | $(M + H)^+ = 424$ | 0.72 min (method A) |

-continued
| Nr. | Structure | Mass signal(s) | $R_f$ Value or $R_t$ |
|---|---|---|---|
| 12 | Obtained as TFA salt | $(M + H)^+ = 451$ | 1.20 min (method C) |
| 16 | Obtained as TFA salt | $(M + H)^+ = 493$ | 0.73 min (method B) |
| 19 | Obtained as TFA salt | $(M + H)^+ = 418$ | 0.71 min (method B) |
| 20 | Obtained as TFA salt | $(M + H)^+ = 404$ | 0.70 min (method B) |
Example 5
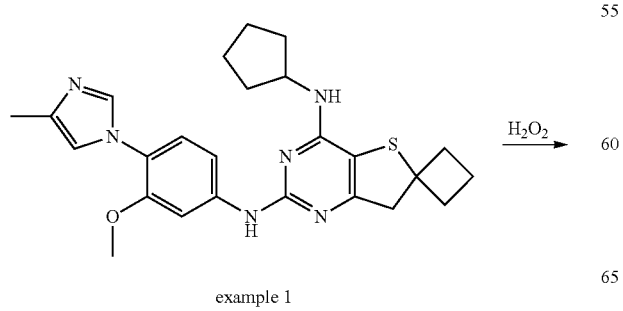
example 1
-continued
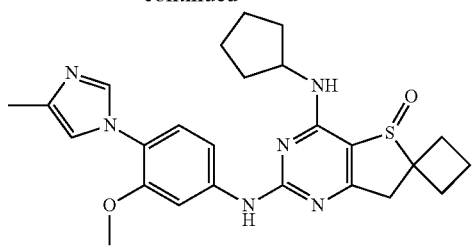
example 5
To a mixture of 19.0 mg (21.0 µmol) of compound example 1 in 205 µL acetic acid is added hydrogen peroxide (1.94 µL, 23.00 µmol, 35% solution in water). After stirring for 4.5 h the mixture is purified directly by HPLC to give the product as TFA salt.

$C_{25}H_{30}N_6O_2S$ (468.72)

Mass spectrometry (ESI$^+$): m/z=137 [M+H]$^+$
HPLC (Method A): Retention time=0.60 min.

In analogy to the preparation of example 6 the following compounds are obtained:

| Nr. | Structure | Mass signal(s) | $R_f$ Value or $R_t$ |
|---|---|---|---|
| 8 | (structure) Obtained as acetate salt | (M + H)$^+$ = 481 | 0.56 min (method A) |
| 9 | (structure) | (M + H)$^+$ = 424 | 0.70 min (method A) |
| 14 | (structure) Obtained as TFA salt | (M + H)$^+$ = 507 | 1.19 min (method C) |
| 15 | (structure) Obtained as TFA salt | (M + H)$^+$ = 467 | 1.08 min (method C) |
| 17 | (structure) Obtained as TFA salt | (M + H)$^+$ = 509 | 0.70 min (method B) |

| Nr. | Structure | Mass signal(s) | $R_f$-Value or $R_t$ |
|---|---|---|---|
| 22 | Obtained as TFA salt | $(M + H)^+ = 420$ | 0.68 min (method B) |
| 23 | Obtained as TFA salt | $(M + H)^+ = 434$ | 0.66 min (method B) |

Example 10

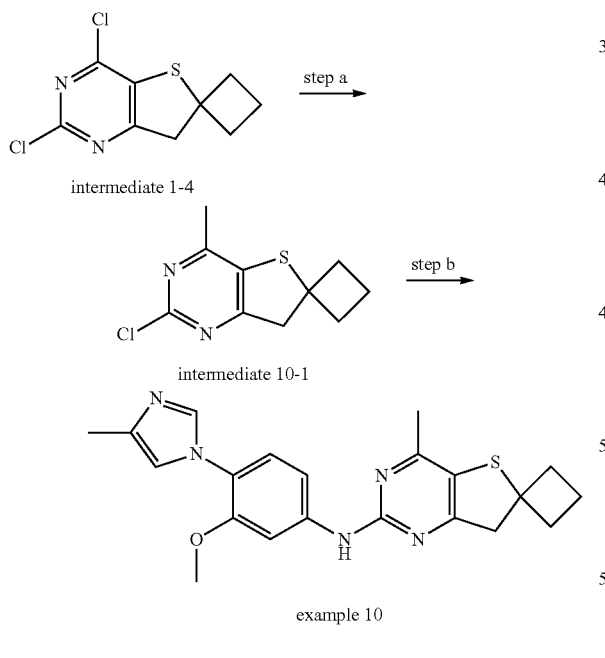

Step a

Intermediate 10-1

To a mixture of 96 mg (388 µmol) of intermediate 1-4 and 41 mg (117 µmol) iron (III) acetylacetonate in a mixture of 2 mL THF and 150 µL NMP is added methyl magnesium chloride (140 µL, 427 µmol, 3N solution in THF) at 0° C. After stirring for 0.5 h the mixture is diluted with water and extracted with ethyl acetate. The aqueous phase is extracted with ethyl acetate and the organic phases are combined, dried over sodium sulfate, filtered and concentrated in vacuo. The crude product is purified by HPLC.

$C_{10}H_{11}N_2ClS$ (226.73)

Mass spectrometry (ESI$^+$): m/z=227 [M+H]$^+$

HPLC (Method C): Retention time=1.38 min.

Step b

Example 10

50.0 mg (221.0 µmol) of intermediate 10-1,3-methoxy-4-(4-methyl-imidazol-1-yl)-phenylamine 58.3 mg (287.0 µmol), 51.3 mg (397.0 µmol) cesium carbonate, 5.0 mg (22.0 µmol) palladium(II) acetate and 25.5 mg (44.0 µmol) Xantphos are mixed together in 2 mL 1,4-dioxane. The reaction is heated by microwave irradiation for 6 h at 120° C. After cooling the mixture is diluted with methanol and purified directly by HPLC to give the product as TFA salt.

$C_{21}H_{23}N_5OS$ (393.51)

Mass spectrometry (ESI$^+$): m/z=394 [M+H]$^+$

HPLC (Method C): Retention time=1.24 min.

In analogy to the preparation of example 10 the following compounds are obtained:

| Nr. | Structure | Mass signal(s) | $R_f$ Value or $R_t$ |
|---|---|---|---|
| 18 | 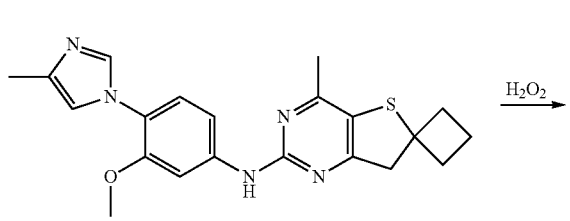 Obtained as acetate salt | $(M + H)^+ = 450$ | 1.04 min (method C) |

Example 11

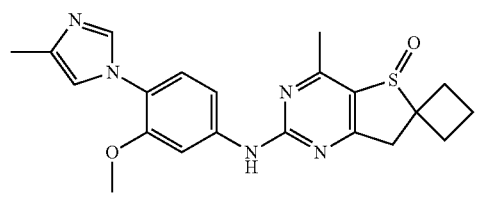

example 10

→ $H_2O_2$ →

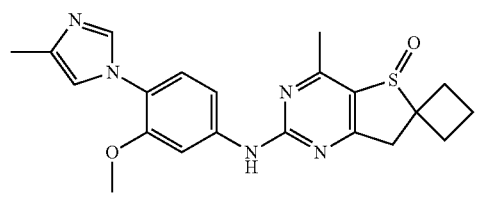

example 11

To a mixture of 45.0 mg (89.0 µmol) of compound example 10 in 1 mL acetic acid is added hydrogen peroxide (8.4 µL, 98.0 µmol, 35% solution in water). After stirring for 2 h the mixture is taken up in DCM, separated from the aqueous phase and concentrated in vacuo to give crude material which is purified by HPLC to give the title compound as TFA salt.

$C_{21}H_{23}N_5O_2S$ (409.51)

Mass spectrometry (ESI$^+$): m/z=410 [M+H]$^+$

HPLC (Method C): Retention time=0.60 min.

In analogy to the preparation of example 11 the following compounds are obtained:

Example 13

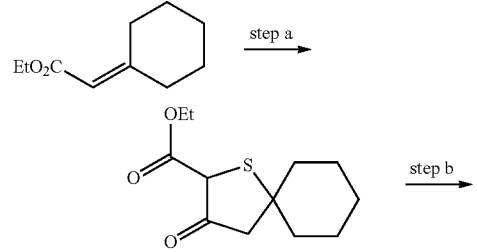

intermediate 13-1

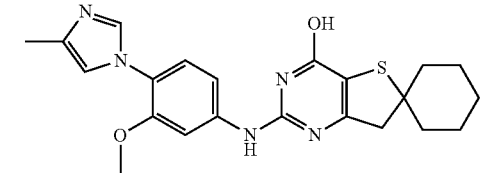

intermediate 13-2

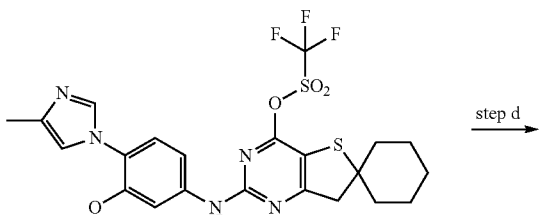

intermediate 13-3

| Nr. | Structure | Mass signal(s) | $R_f$ Value or $R_t$ |
|---|---|---|---|
| 21 | Obtained as acetate salt | $(M + H)^+ = 466$ | 1.09 min (method C) |

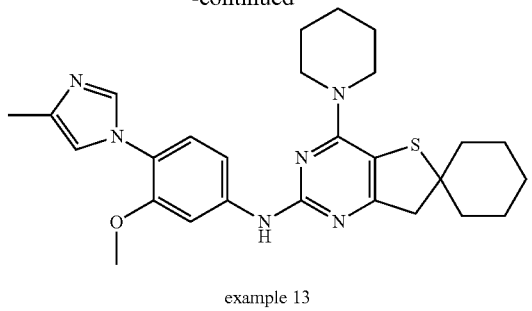

example 13

Step a

Intermediate 13-1

23.0 mL (209.5 mmol) Mercapto acetic acid ethyl ester and 1.4 mL (14.0 mmol) piperidine are mixed together in ethanol (150 mL). After addition of 23.5 g cyclohexyliden acetic acid ethyl ester (139.7 mmol) the mixture is stirred for 20 h. The reaction mixture is cooled to −25° C. and carefully added to 300 mL of a freshly prepared sodium ethanolate solution (6.42 g sodium metal (279.4 mmol) dissolved in 300 mL dry ethanol) at −25° C. After stirring for 2 h the mixture is quenched by slow addition of 16.7 mL (293.4 mmol) glacial acetic acid and warmed up to room temperature. Then the reaction mixture is concentrated in vacuo to give crude product that is purified by MPLC (silica gel, CH/Ethyl acetate 95:5).

$C_{12}H_{18}O_3S$ (242.34)
Mass spectrometry (ESI$^+$): m/z=243 [M+H]$^+$
TLC (silica gel, CH/ethyl acetate 4:1): $R_f$=0.73

Step b

Intermediate 13-2

270.0 mg (1.1 mmol) N-[3-Methoxy-4-(4-methyl-imidazol-1-yl)-phenyl]-guanidine (prepared in analogy to WO2009/087127) and 266.8 mg (1.1 mmol) 3-oxo-1-thiaspiro[4.5]decane-2-carboxylic acid ethyl ester (intermediate 13-1) are mixed together in pyridine (1.3 mL) and are heated under microwave irradiation at 130° C. for 15 min. The reaction mixture is cooled to RT, diluted with methanol, acidified with TFA and purified directly by HPLC to give the product as TFA salt.

$C_{22}H_{25}N_5O_2S$ (423.54)
Mass spectrometry (ESI$^+$): m/z=424 [M+H]$^+$
HPLC (Method C): Retention time=1.16 min.

Step c

Intermediate 13-3

56.5 mg (158.0 µmol) N-phenyl-trifluoromethanesulfonimide are added to a mixture of 85 mg (158.0 µmol) of intermediate 13-2 and 23.6 µL (158.0 µmol) DBU in DCM (1.1 mL). After 5 min the reaction mixture is poured into brine. The organic phase is separated and concentrated to give the crude product which is purified by MPLC (silica gel, gradient DCM/methanol 100:0 to 98:2).

$C_{23}H_{24}F_3N_5O_4S_2$ (555.60)
Mass spectrometry (ESI$^+$): m/z=556 [M+H]$^+$
HPLC (Method C): Retention time=1.48 min.

Step d

Example 13

57.0 mg (103.0 µmol) of intermediate 13-3 and 12.2 µL (123.0 µmol) piperidine are mixed together in a mixture of 1,4-dioxane (3.0 mL) and DMF (150.0 µL). After 1 h the reaction mixture is concentrated in vacuo, taken up in ethyl acetate and subsequently washed with saturated aqueous NaHCO$_3$ solution. The organic phase is dried over sodium sulfate and concentrated in vacuo to give the crude product which is purified by HPLC.

$C_{27}H_{34}N_6OS$ (490.68)
Mass spectrometry (ESI$^+$): m/z=491 [M+H]$^+$
HPLC (Method C): Retention time=1.25 min.

The invention claimed is:
1. A compound of the formula I

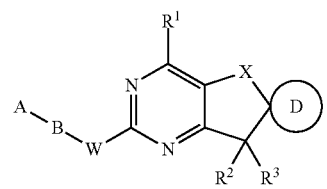

wherein
A is selected from the group A$^a$ consisting of
a heteroaryl group with 5 or 6 ring atoms containing one to three heteroatoms independently selected from N, O, S,
wherein above mentioned heteroaryl groups may optionally be substituted with 1 or 2 substituents independently selected from the group consisting of halogen, cyano, C$_{1-6}$-alkyl- which is optionally fluorinated with 1 to 13 fluorine atoms, C$_{3-6}$-cycloalkyl-, C$_{1-4}$-alkyl-O—C$_{1-3}$-alkyl-, C$_{1-4}$-alkyl-O— which is optionally fluorinated with 1 to 9 fluorine atoms and (C$_{1-4}$-alkyl)$_3$Si—;
B is selected from the group B$^a$ consisting of

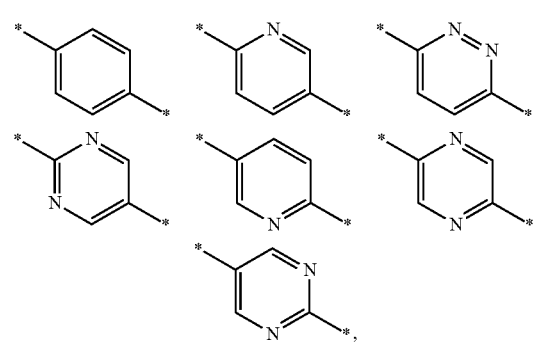

wherein above mentioned phenyl-, pyridinyl-, pyrimidinyl-, pyridazinyl and pyrazinyl groups may optionally be substituted with 1 or 2 substituents independently selected from the group consisting of HO—, halogen, cyano, C$_{1-6}$-alkyl- which is optionally fluorinated with 1 to 13 fluorine atoms, C$_{3-6}$-cycloalkyl-O— and C$_{1-6}$-alkyl-O— which is optionally fluorinated with 1 to 13 fluorine atoms;

D is selected from the group $D^a$ consisting of
- a mono- or bicyclic carbocyclus consisting of 3 to 10 carbon atoms wherein one of the rings may be an aromatic ring, or
- a 4- to 12-membered mono-, bicyclic or bridged heterocyclyl group, wherein above mentioned ring $D^a$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, heterocyclyl, aryl, aryl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, aryl-C(O)—, $C_{1-4}$-alkyl-O—C(O)—, $(C_{1-4}$-alkyl$)_2$N—C(O)—, HO—, oxo, $C_{1-6}$-alkyl-O— which is optionally fluorinated with 1 to 13 fluorine atoms, $C_{3-6}$-cycloalkyl-O—, heterocyclyl-O—, aryl-O—, heteroaryl-O—, $H_2N$—, $(C_{1-4}$-alkyl$)_2$N—, azetidinyl, pyrrolidinyl and $(C_{1-4}$-alkyl)$(C_{1-3}$-alkyl-C(O))N—, wherein above mentioned aryl-C(O)—, aryl-O—, aryl, aryl-$C_{1-3}$-alkyl-, heteroaryl, heteroaryl-$C_{1-3}$-alkyl- and heteroaryl-O— groups may optionally be substituted with 1 to 3 substituents independently selected from the group consisting of HO—, $C_{1-4}$-alkyl-O—, $F_3$CO—, $F_3$C—, $F_2$HCO—, $FH_2$CO—, heterocyclyl-O—, cyano, halogen, $F_5S$—, $(C_{1-4}$-alkyl$)_3$Si—, nitro, $H_2N$—, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl-which is optionally fluorinated with 1 to 13 fluorine atoms;

W is selected from the group $W^a$ consisting of
—$(R^7)$N— and —O—;

X is selected from the group $X^a$ consisting of
—S—, —S(O)— and —S(O)$_2$—;

$R^1$ is selected from the group $R^{1a}$ consisting of
H, $C_{1-6}$-alkyl-, $C_{2-6}$-alkenyl-, $C_{2-6}$-alkynyl-, carbocyclyl, carbocyclyl-$C_{1-3}$-alkyl-, C-linked heterocyclyl, heterocyclyl-$C_{1-3}$-alkyl-, aryl, aryl-$C_{1-3}$-alkyl-, heteroaryl, heteroaryl-$C_{1-3}$-alkyl-, $R^4R^5N$—, $R^4R^5N$—$C_{1-3}$-alkyl- and $R^4$O—, wherein above mentioned $C_{2-6}$-alkenyl-, $C_{2-6}$-alkynyl-, C-linked heterocyclyl, heterocyclyl-$C_{1-3}$-alkyl-, aryl, aryl-$C_{1-3}$-alkyl-, heteroaryl and heteroaryl-$C_{1-3}$-alkyl-groups may optionally be substituted with 1 to 3 substituents independently selected from the group consisting of HO—, $C_{1-4}$-alkyl-O—, $F_3$CO—, $F_2$HCO—, $FH_2$CO—, heterocyclyl-O—, cyano, halogen, $F_5S$—, $(C_{1-4}$-alkyl$)_3$Si—, nitro, $H_2N$—, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms, and wherein above mentioned $C_{1-6}$-alkyl-, carbocyclyl and carbocyclyl-$C_{1-3}$-alkyl-groups may optionally be substituted with 1 to 3 substituents independently selected from the group consisting of halogen, cyano, HO—, oxo, $C_{1-6}$-alkyl-, $C_{1-6}$-alkyl-O—, $C_{3-6}$-cycloalkyl-O—, oxetanyl-O—, tetrahydrofuryl-O— and tetrahydropyranyl-O—;

$R^2$, $R^3$ are selected independently of each other from the group $R^{2a}/R^{3a}$ consisting of
H, halogen, $C_{1-6}$-alkyl-, $C_{3-6}$-cycloalkyl-, aryl, aryl-$C_{1-3}$-alkyl-, HO—, $C_{1-6}$-alkyl-O—, $C_{3-6}$-cycloalkyl-O—, wherein above mentioned aryl, and the aryl moiety of the aryl-$C_{1-3}$-alkyl-group may optionally be substituted with 1 to 3 substituents independently selected from the group consisting of HO—, $C_{1-4}$-alkyl-O—, heterocyclyl-O—, cyano, halogen, $F_5S$—, $(C_{1-4}$-alkyl$)_3$Si—, nitro, $H_2N$—, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms, and wherein the alkyl moieties of above mentioned $C_{1-6}$-alkyl-, $C_{3-6}$-cycloalkyl-, aryl-$C_{1-3}$-alkyl-, $C_{1-6}$-alkyl-O— and $C_{3-6}$-cycloalkyl-O-groups may optionally be substituted with 1-13 fluorine atoms, or $R^{2a}$ and $R^{3a}$ form together with the carbon atom to which they are attached an oxo group;

$R^4$, $R^5$ are selected independently of each other from the group $R^{4a}/R^{5a}$ consisting of
H, $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl-, heterocyclyl-O—$C_{2-4}$-alkyl-, aryl, aryl-$C_{1-3}$-alkyl-, aryl-O—$C_{2-3}$-alkyl-, heteroaryl, heteroaryl-$C_{1-3}$-alkyl- and heteroaryl-O—$C_{2-3}$-alkyl-, wherein above mentioned $C_{1-6}$-alkyl-, carbocyclyl, carbocyclyl-$C_{1-3}$-alkyl-, carbocyclyl-O—$C_{2-4}$-alkyl-, heterocyclyl, heterocyclyl-$C_{1-6}$-alkyl- or heterocyclyl-O—$C_{2-4}$-alkyl- groups may optionally be substituted with 1 to 3 substituents independently selected from the group consisting of halogen, cyano, HO—, oxo, $C_{1-4}$-alkyl-O— which is optionally fluorinated with 1 to 9 fluorine atoms, $C_{1-4}$-alkyl-O—C(O)—, HO—$C_{1-4}$-alkyl-, $C_{1-4}$-alkyl-O—$C_{1-4}$-alkyl-, heterocyclyl, $(C_{1-4}$-alkyl$)_2$N—, $(C_{1-3}$-alkyl$)_2$N—C(O)—, and $C_{1-6}$-alkyl- which is optionally fluorinated with 1 to 13 fluorine atoms, wherein above mentioned aryl-, aryl-$C_{1-3}$-alkyl-, aryl-O—$C_{2-3}$-alkyl-, heteroaryl-, heteroaryl-$C_{1-3}$-alkyl- and heteroaryl-O—$C_{2-3}$-alkyl- groups may optionally be substituted with 1 to 3 substituents independently selected from the group consisting of HO—, $C_{1-4}$-alkyl-O—, $F_3$CO—, $F_2$HCO—, $FH_2$CO—, heterocyclyl-O—, cyano, halogen, $F_5S$—, $(C_{1-4}$-alkyl$)_3$Si—, nitro, $(R^6)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms, or $R^{4a}$ and $R^{5a}$ form together with the nitrogen atom to which they are attached a 4-12-membered mono-, bicyclic or bridged ring system optionally containing one or two double bonds and/or one aromatic ring and optionally containing one or two additional heteroatoms selected from the group consisting of —O—, —S—, —S(O)—, —S(O)$_2$—, —N($R^6$)—, wherein 2 geminal hydrogen atoms of the 4-12-membered mono- or bicyclic ring system may be replaced by a —(CH$_2$)$_{1-5}$— group and
  wherein one —(CH$_2$)— group of the —(CH$_2$)$_{1-5}$— group may be replaced by —O— or —N($R^6$)— and wherein above mentioned 4-12-membered mono-, bicyclic or bridged ring system may optionally be substituted with 1 or 2 substituents independently selected from the group consisting of halogen, cyano, aryl, heteroaryl, aryl-$C_{1-3}$-alkyl-, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, $C_{1-4}$-alkyl-O—C(O)—, HO—$C_{1-4}$-alkyl-, $C_{1-4}$-alkyl-O—$C_{1-4}$-alkyl-, $C_{3-6}$-cycloalkyl-O—$C_{1-4}$-alkyl-, heterocyclyl-O—, heterocyclyl-O—$C_{1-4}$-alkyl-, aryl-O—, heteroaryl-O— and $(R^6)_2N$—,
wherein the directly above mentioned aryl, aryl-$C_{1-3}$-alkyl-, aryl-O—, heteroaryl-O—, and heteroaryl groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, amino, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl- which is optionally fluorinated with 1 to 13 fluorine atoms;
$R^6$ is selected independently of each other from the group $R^{6a}$ consisting of
H, $C_{1-6}$-alkyl-, $C_{3-6}$-cycloalkyl, heterocyclyl, heteroaryl, HC(O)—, $C_{1-6}$-alkyl-C(O)—, $C_{3-6}$-cycloalkyl-C(O)—, aryl-C(O)—, $C_{1-4}$-alkyl-O—C(O)— and $(C_{1-4}$-alkyl$)_2N$—C(O)—,
wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms and
wherein the above mentioned aryl-C(O)— and heteroaryl group may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3Si$—, nitro, amino, $(C_{1-4}$-alkyl$)_2N$—, $(H_2N)$—C(O)—, $(C_{1-4}$-alkyl)-HN—C(O)—, $(C_{1-4}$-alkyl$)_2N$—C(O)—, $C_{1-4}$-alkyl-O—$C_{1-4}$-alkyl- and $C_{1-6}$-alkyl-which is optionally fluorinated with 1 to 13 fluorine atoms;
$R^7$ is selected independently of each other from the group $R^{7a}$ consisting of
H, $C_{1-6}$-alkyl-, $C_{1-6}$-alkyl-C(O)— and $C_{1-6}$-alkyl-O—C(O)—,
or a salt thereof.

2. A compound according to claim 1, wherein
A is selected from the group $A^b$ consisting of

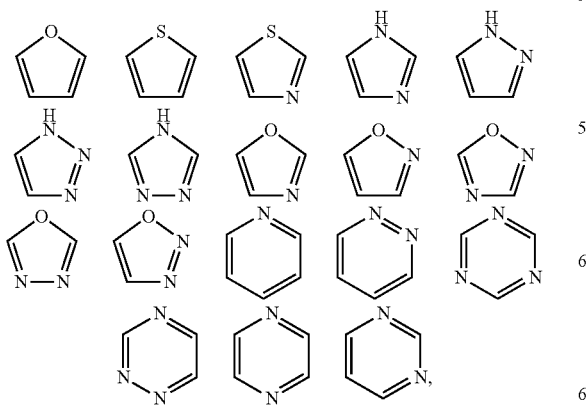

wherein above mentioned groups may optionally be substituted with 1 or 2 substituents independently selected from the group consisting of halogen, cyano, and $C_{1-6}$-alkyl- which is optionally fluorinated with 1 to 13 fluorine atoms.

3. A compound according to claim 1, wherein
A is selected from the group $A^c$ consisting of

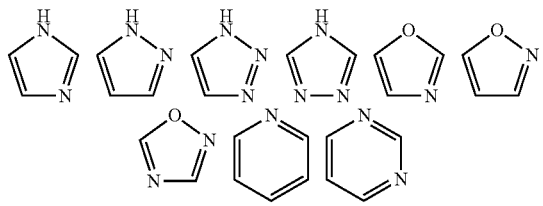

wherein above mentioned groups may optionally be substituted with 1 or 2 substituents independently selected from the group consisting of halogen and $C_{1-3}$-alkyl- which is optionally fluorinated with 1 to 7 fluorine atoms.

4. A compound according to claim 1, wherein
B Is selected from the group $B^b$ consisting of

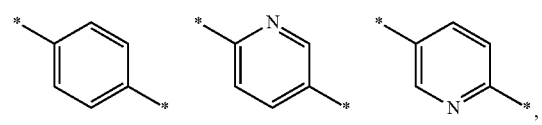

wherein above mentioned phenyl- and pyridinyl-groups may optionally be substituted with 1 or 2 substituents independently selected from the group consisting of HO—, halogen, cyano, $C_{1-6}$-alkyl- which is optionally fluorinated with 1 to 13 fluorine atoms, $C_{3-6}$-cycloalkyl-O— and $C_{1-6}$-alkyl-O— which is optionally fluorinated with 1 to 13 fluorine atoms.

5. A compound according to claim 1, wherein
D is selected from the group $D^b$ consisting of

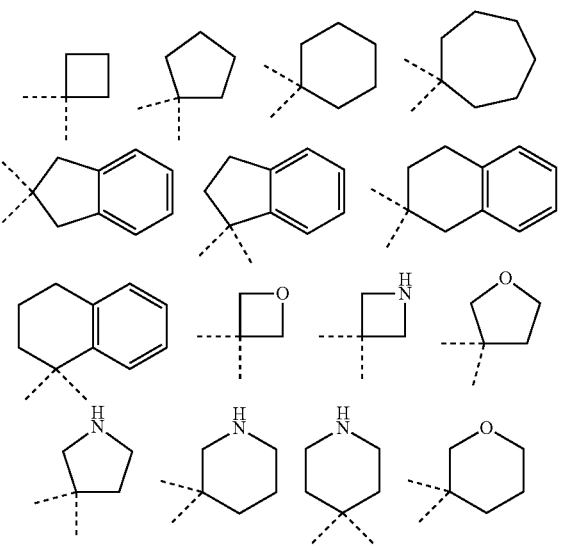

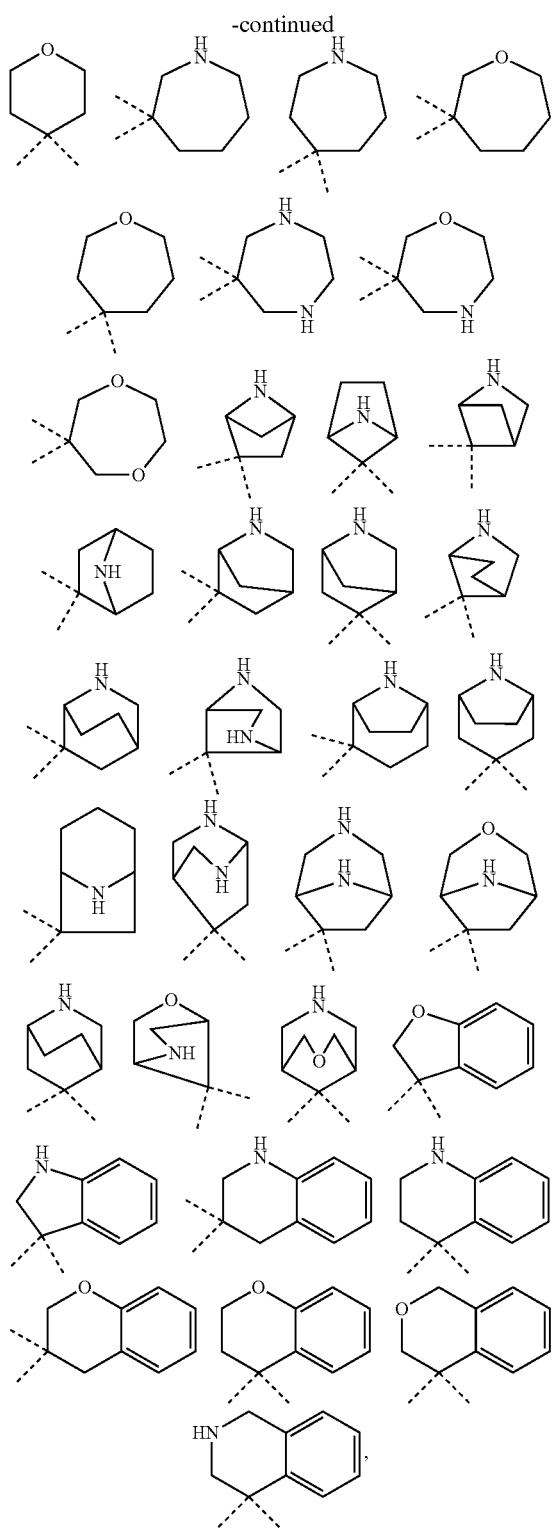

wherein above mentioned ring system $D^b$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, heterocyclyl, aryl, aryl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, aryl-C(O)—, $C_{1-4}$-alkyl-O—C(O)—, ($C_{1-4}$-alkyl)$_2$N—C(O)—, HO—, oxo, $C_{1-6}$-alkyl-O— which is optionally fluorinated with 1 to 13 fluorine atoms, $C_{3-6}$-cycloalkyl-O—, heterocyclyl-O—, aryl-O—, heteroaryl-O—, $H_2$N—, ($C_{1-4}$-alkyl)$_2$N—, azetidinyl, pyrrolidinyl and ($C_{1-4}$-alkyl)($C_{1-3}$-alkyl-C(O))N—, wherein above mentioned aryl-C(O)—, aryl-O—, aryl, aryl-$C_{1-3}$-alkyl-, heteroaryl, heteroaryl-$C_{1-3}$-alkyl- and heteroaryl-O— groups may optionally be substituted with 1 to 3 substituents independently selected from the group consisting of HO—, $C_{1-4}$-alkyl-O—, $F_3$CO—, $F_3$C—, $F_2$HCO—, $FH_2$CO—, heterocyclyl-O—, cyano, halogen, $F_5$S—, ($C_{1-4}$-alkyl)$_3$Si—, nitro, $H_2$N—, ($C_{1-4}$-alkyl)$_2$N—, ($H_2$N)—C(O)—, ($C_{1-4}$-alkyl)-HN—C(O)—, ($C_{1-4}$-alkyl)$_2$N—C(O)—, $C_{1-4}$-alkyl-O—$C_{1-4}$-alkyl- and $C_{1-6}$-alkyl- which is optionally fluorinated with 1 to 13 fluorine atoms.

6. A compound according to claim 1, wherein
D is selected from the group $D^c$ consisting of

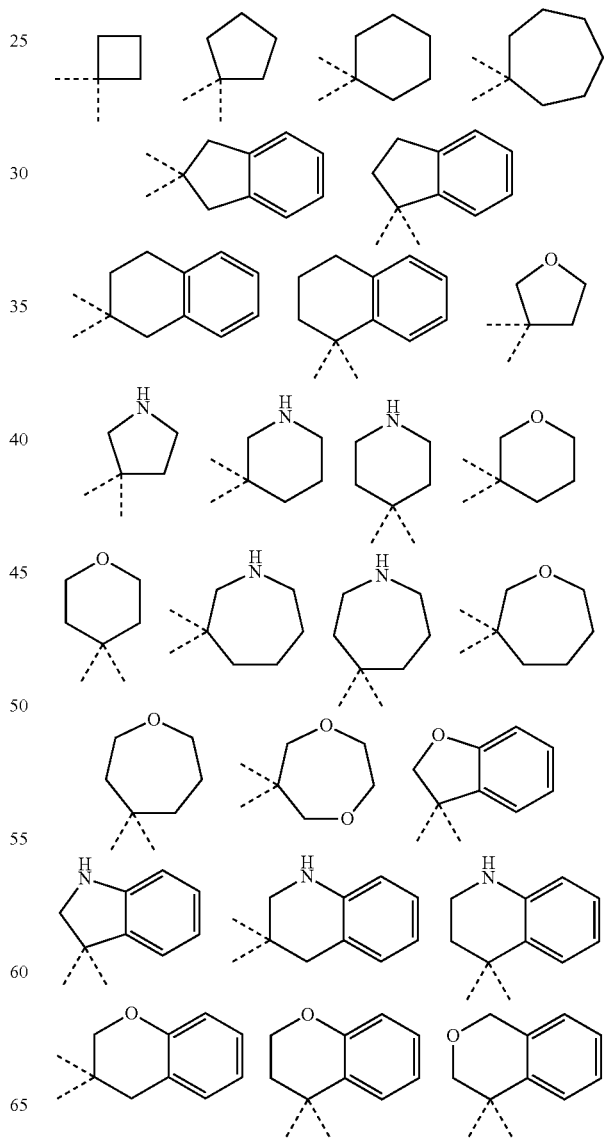

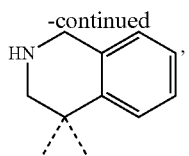

wherein above mentioned ring $D^c$ may optionally be substituted with 1 to 4 substituents independently selected from the group consisting of halogen, cyano, $C_{1-6}$-alkyl- which is optionally fluorinated with 1 to 13 fluorine atoms, $C_{3-6}$-cycloalkyl-, oxetanyl, tetrahydrofuryl, tetrahydropyranyl, phenyl, phenyl-$C_{1-3}$-alkyl-, heteroaryl, heteroaryl-$C_{1-3}$-alkyl-, HC(O)—, $C_{1-6}$-alkyl-C(O)—, $C_{3-6}$-cycloalkyl-C(O)—, phenyl-C(O)—, $C_{1-4}$-alkyl-O—C(O)—, $(C_{1-4}$-alkyl$)_2$N—C(O)—, HO—, oxo, $C_{1-6}$-alkyl-O— which is optionally fluorinated with 1 to 13 fluorine atoms, $C_{3-6}$-cycloalkyl-O—, oxetanyl-O—, tetrahydrofuryl-O—, tetrahydropyranyl-O—, phenyl-O—, heteroaryl-O—, $H_2N$—, $(C_{1-4}$-alkyl$)_2$N—, azetidinyl, pyrrolidinyl and $(C_{1-4}$-alkyl$)(C_{1-3}$-alkyl-C(O))N—, wherein above mentioned phenyl, phenyl-$C_{1-3}$-alkyl-, heteroaryl-$C_{1-3}$-alkyl-, phenyl-C(O)—, phenyl-O—, heteroaryl- and heteroaryl-O-group may optionally be substituted with 1 to 3 substituents independently selected from the group consisting of HO—, $C_{1-4}$-alkyl-O—, $F_3C$—, $F_3CO$—, $F_2HCO$—, $FH_2CO$—, oxetanyl-O—, tetrahydrofuryl-O—, tetrahydropyranyl-O—, cyano, halogen, $F_5S$—, $(C_{1-4}$-alkyl$)_3$Si—, nitro, $H_2N$—, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms.

7. A compound according to claim 1, wherein
X is selected from the group $X^b$ consisting of
—S—, and —S(O)—.

8. A compound according to claim 1, wherein
$R^1$ is selected from the group $R^{1b}$ consisting of
H, $C_{1-6}$-alkyl-, $C_{3-7}$-cycloalkyl-, $C_{3-7}$-cycloalkyl-$C_{1-3}$-alkyl-, C-linked heterocyclyl, heterocyclyl-$C_{1-3}$-alkyl-, aryl-$C_{1-3}$-alkyl-, heteroaryl-$C_{1-3}$-alkyl-, $R_4R_5N$—, $R_4R_5N$—$C_{1-3}$-alkyl- and $R_4O$—,
wherein above mentioned C-linked heterocyclyl, heterocyclyl-$C_{1-3}$-alkyl-, aryl-$C_{1-3}$-alkyl- and heteroaryl-$C_{1-3}$-alkyl-groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3$Si—, nitro, $H_2N$—, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms, and
wherein above mentioned $C_{1-6}$-alkyl-, $C_{3-7}$-cycloalkyl- and $C_{3-7}$-cycloalkyl-$C_{1-3}$-alkyl-groups may optionally be substituted with 1 to 3 substituents independently selected from the group consisting of halogen, cyano, HO—, oxo, $C_{1-6}$-alkyl-, $C_{1-6}$-alkyl-O—, $C_{3-6}$-cycloalkyl-O—, oxetanyl-O—, tetrahydrofuryl-O— and tetrahydropyranyl-O—.

9. A compound according to claim 1, wherein
$R^1$ is selected from the group $R^{1c}$ consisting of
H, $R^4R^5N$—, $R^4R^5N$—$C_{1-3}$-alkyl- and $R^4O$—.

10. A compound according to claim 1, wherein
$R^1$ is selected from the group $R^{1d}$ consisting of
H, $C_{1-6}$-alkyl-, $C_{3-7}$-cycloalkyl-, $C_{3-7}$-cycloalkyl-$C_{1-3}$-alkyl-, C-linked heterocyclyl, heterocyclyl-$C_{1-3}$-alkyl-, aryl-$C_{1-3}$-alkyl-, heteroaryl-$C_{1-3}$-alkyl-, $R^4R^5N$— and $R^4R^5N$—$C_{1-3}$-alkyl-,
wherein above mentioned C-linked heterocyclyl, heterocyclyl-$C_{1-3}$-alkyl-, aryl-$C_{1-3}$-alkyl- and heteroaryl-$C_{1-3}$-alkyl-groups may optionally be substituted with 1 to 3 substituents independently selected from the group consisting of HO—, $C_{1-4}$-alkyl-O—, $F_3CO$—, $F_2HCO$—, $FH_2CO$—, heterocyclyl-O—, cyano, halogen, $F_5S$—, $(C_{1-4}$-alkyl$)_3$Si—, nitro, $H_2N$—, $(C_{1-4}$-alkyl$)_2$N—, $(H_2N)$—C(O)—, $(C_{1-4}$-alkyl)-HN—C(O)—, $(C_{1-4}$-alkyl$)_2$N—C(O)—, $C_{1-4}$-alkyl-O—$C_{1-4}$-alkyl- and $C_{1-6}$-alkyl- which is optionally fluorinated with 1 to 13 fluorine atoms, and
wherein above mentioned $C_{1-6}$-alkyl-, $C_{3-7}$-cycloalkyl- and $C_{3-7}$-cycloalkyl-$C_{1-3}$-alkyl-groups may optionally be substituted with 1 to 3 substituents independently selected from the group consisting of halogen, cyano, HO—, oxo, $C_{1-6}$-alkyl-, $C_{1-6}$-alkyl-O—, $C_{3-6}$-cycloalkyl-O—, oxetanyl-O—, tetrahydrofuryl-O— and tetrahydropyranyl-O—.

11. A compound according to claim 1, wherein
$R^2$, $R^3$ are selected independently of each other from the group $R^{2b}/R^{3b}$ consisting of
H, phenyl,
wherein above mentioned phenyl group may optionally be substituted with 1 to 3 substituents independently selected from the group consisting of $C_{1-4}$-alkyl-O—, cyano, halogen $F_3C$— and $C_{1-6}$-alkyl-.

12. A compound according to claim 1, wherein
$R^4$, $R^5$ are selected independently of each other from the group $R^{4b}/R^{5b}$ consisting of
H, $C_{1-6}$-alkyl-, $C_{3-7}$-cycloalkyl, $C_{3-7}$-cycloalkyl-$C_{1-3}$-alkyl-, $C_{3-7}$-cycloalkyl-O—$C_{2-4}$-alkyl-, heterocyclyl, heterocyclyl-$C_{1-6}$-alkyl-, aryl, aryl-$C_{1-3}$-alkyl-, aryl-O—$C_{2-3}$-alkyl-, heteroaryl and heteroaryl-$C_{1-3}$-alkyl-,
wherein above mentioned $C_{1-6}$-alkyl-, $C_{3-7}$-cycloalkyl-, $C_{3-7}$-cycloalkyl-$C_{1-3}$-alkyl-, $C_{3-7}$-cycloalkyl-O—$C_{2-4}$-alkyl-, heterocyclyl or heterocyclyl-$C_{1-6}$-alkyl- groups may optionally be substituted with 1 to 3 substituents independently selected from the group consisting of fluoro, HO—, oxo, $C_{1-4}$-alkyl-O— which is optionally fluorinated with 1 to 9 fluorine atoms, HO—$C_{1-4}$-alkyl-, $C_{1-4}$-alkyl-O—$C_{1-4}$-alkyl-, heterocyclyl, $(C_{1-3}$-alkyl$)_2$N—C(O)—, and $C_{1-6}$-alkyl- which is optionally fluorinated with 1 to 13 fluorine atoms,
wherein above mentioned aryl-, aryl-$C_{1-3}$-alkyl-, aryl-O—$C_{2-3}$-alkyl-, heteroaryl- and heteroaryl-$C_{1-3}$-alkyl- groups may optionally be substituted with 1 to 3 substituents independently selected from the group consisting of $C_{1-4}$-alkyl-O—, $F_3CO$—, $F_2HCO$—, $FH_2CO$—, cyano, halogen, $(C_{1-4}$-alkyl$)_2$N—C(O)—, and $C_{1-6}$-alkyl- which is optionally fluorinated with 1 to 13 fluorine atoms, or
$R^{4b}$ and $R^{5b}$ form together with the nitrogen atom to which they are attached a 4-12-membered mono-, bicyclic or bridged ring system optionally containing one double bond and/or one aromatic ring and optionally containing one additional heteroatom selected from the group consisting of —O—, —N($R^6$)—, wherein 2 geminal hydrogen atoms of the 4-12-membered mono- or bicyclic ring may be replaced by a —$(CH_2)_{1-5}$— group and wherein one —$(CH_2)$— group of the —$(CH_2)_{1-5}$— group may be replaced by —O— or —N($R^6$)— and wherein above mentioned 4-12-membered mono-, bicyclic or bridged ring system may optionally be substituted with 1 or 2 substituents independently selected from the group consisting of fluoro, aryl, heteroaryl, $C_{1-6}$-alkyl- which is optionally fluorinated with 1 to 13 fluorine atoms, heterocyclyl, HO—, oxo, $C_{1-6}$-alkyl-O—, $C_{3-6}$-cycloalkyl-O—, HO—$C_{1-4}$-alkyl-, $C_{1-4}$-alkyl-O—$C_{1-4}$-alkyl-, heterocyclyl-O— and $(R^6)_2$N—, wherein the directly above mentioned aryl and heteroaryl groups may optionally be substituted with 1 to 3 substituents independently selected from the group consisting of $C_{1-4}$-alkyl-O—, $F_3$CO—, $F_2$HCO—, $FH_2$CO—, cyano, halogen, $(C_{1-4}$-alkyl$)_2$N—C(O)— and $C_{1-6}$-alkyl-which is optionally fluorinated with 1 to 13 fluorine atoms.

13. A compound according to claim 1, wherein $R^6$ is selected independently of each other from the group $R^{6b}$ consisting of H, $C_{1-6}$-alkyl-, $C_{3-6}$-cycloalkyl, oxetanyl, tetrahydrofuryl, tetrahydropyranyl, pyridinyl, pyrimidinyl, pyridazinyl, pyrazinyl, triazinyl, thiazolyl, oxadiazolyl, oxazolyl, HC(O)—, $C_{1-6}$-alkyl-C(O)—, $C_{3-6}$-cycloalkyl-C(O)—, phenyl-C(O)—, $C_{1-4}$-alkyl-O—C(O)— and $(C_{1-4}$-alkyl$)_2$N—C(O)—, wherein above mentioned $C_{1-6}$-alkyl-, $C_{3-6}$-cycloalkyl-, $C_{1-6}$-alkyl-C(O)— and $C_{3-6}$-cycloalkyl-C(O)— groups may optionally be substituted with 1-13 fluorine atoms and wherein the aforementioned phenyl-C(O)—, pyridinyl, pyrimidinyl, pyridazinyl, pyrazinyl, triazinyl, thiazolyl oxadiazolyl and oxazolyl groups may optionally be substituted with 1 to 3 substituents independently selected from the group consisting of $C_{1-4}$-alkyl-O—, $F_3$C—, $F_3$CO—, $F_2$HCO—, $FH_2$CO—, cyano, halogen, and $C_{1-3}$-alkyl-.

14. A pharmaceutically acceptable salt of a compound according to claim 1.

15. A pharmaceutical composition comprising a compound according to claim 1, or a pharmaceutically acceptable salt thereof, together with a pharmaceutically acceptable carrier.

16. A method for treating Alzheimer's disease which comprises administering to a host suffering from the same a therapeutically effective amount of a compound according to claim 1, or a pharmaceutically acceptable salt thereof.

* * * * *